United States Patent
Wong et al.

(10) Patent No.: US 11,103,555 B2
(45) Date of Patent: *Aug. 31, 2021

(54) COMPOSITIONS AND METHODS FOR REDUCING TUMOR CELL GROWTH AT A SITE OF SOLID TUMOR EXCISION

(71) Applicant: The Pacific Heart, Lung, & Blood Institute, Los Angeles, CA (US)

(72) Inventors: Raymond Wong, Los Angeles, CA (US); Robert Cameron, Los Angeles, CA (US)

(73) Assignee: THE PACIFIC HEART, LUNG, & BLOOD INSTITUTE, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,262

(22) Filed: Dec. 19, 2018

(65) Prior Publication Data
US 2019/0183977 A1 Jun. 20, 2019

Related U.S. Application Data

(63) Continuation of application No. 15/616,393, filed on Jun. 7, 2017, now Pat. No. 10,201,592.

(60) Provisional application No. 62/347,005, filed on Jun. 7, 2016.

(51) Int. Cl.
| | |
|---|---|
| *A61K 38/02* | (2006.01) |
| *A61K 35/28* | (2015.01) |
| *A61K 38/17* | (2006.01) |
| *A61K 38/48* | (2006.01) |
| *A61K 35/00* | (2006.01) |
| *A61K 38/20* | (2006.01) |

(52) U.S. Cl.
CPC ............ *A61K 38/208* (2013.01); *A61K 35/28* (2013.01); *A61K 38/1709* (2013.01); *A61K 38/4873* (2013.01); *C12Y 304/22062* (2013.01); *A61K 35/00* (2013.01)

(58) Field of Classification Search
None
See application file for complete search history.

(56) References Cited

U.S. PATENT DOCUMENTS

| | | |
|---|---|---|
| 8,420,087 B2 | 4/2013 | Gillies et al. |
| 10,201,592 B2 | 2/2019 | Wong et al. |
| 2014/0186375 A1 | 7/2014 | Fewell et al. |
| 2016/0129110 A1 | 5/2016 | Garry et al. |

FOREIGN PATENT DOCUMENTS

| | | |
|---|---|---|
| CN | 101272798 A | 9/2008 |
| CN | 102695517 A | 9/2012 |
| CN | 104160027 A | 11/2014 |
| WO | WO-2016014530 A1 | 1/2016 |

OTHER PUBLICATIONS

Ankrum, J.A. et al. Mesenchymal stem cells: immune evasive, not immune privileged. Nat Biotechnol. 32(3):252-60; 2014.
Barese et al. Regulated Apoptosis of Genetically Modified Hematopoietic Stem and Progenitor Cells Via an Inducible Caspase-9 Suicide Gene in Rhesus Macaques. Stem Cells 33(1):91-100 (2015).
Bitsika, V. et al. Human amniotic fluid-derived mesenchymal stem cells as therapeutic vehicles: a novel approach for the treatment of bladder cancer. Stem Cells Dev. 21(7):1097-111; 2012.
Bourgine, P. et al. Combination of immortalization and inducible death strategies to generate a human mesenchymal stromal cell line with controlled survival. Stem Cell Res. 12(2):584-98; 2014.
Consentius, C. et al. Immunogenicity of allogeneic mesenchymal stromal cells: what has been seen in vitro and in vivo? Regen Med. 10(3):305-15; 2015.
Dembinski, J.L. Tumor stroma engraftment of gene-modified mesenchymal stem cells as anti-tumor therapy against ovarian cancer. Cytotherapy. 15(1):20-32; 2013.
Gao, P. et al. Therapeutic potential of human mesenchymal stem cells producing IL-12 in a mouse xenograft model of renal cell carcinoma. Cancer Lett. 290(2):157-66; 2010.
Griffin, M.D., et al. Immunological aspects of allogeneic mesenchymal stem cell therapies. Hum Gene Ther. 21(12):1641-55; 2010.
Hung, SC et al. Mesenchymal stem cell targeting of microscopic tumors and tumor stroma development monitored by noninvasive in vivo positron emission tomography imaging. Clin Cancer Res. 11(21):7749-56; 2005.
Kidd, S. et al. Mesenchymal stromal cells alone or expressing interferon-beta suppress pancreatic tumors in vivo, an effect countered by anti-inflammatory treatment. Cytotherapy. Sep. 2010;12(5):615-25.
Lasek, W. et al. Interleukin 12: still a promising candidate for tumor immunotherapy? Cancer Immunol Immunother. 63(5):419-35; 2014.
Lathrop, M.J. et al. Antitumor effects of TRAIL-expressing mesenchymal stromal cells in a mouse xenograft model of human mesothelioma. Cancer Gene Therapy 22:44-54 (2015).
Le Blanc, K. et al. Immunomodulation by mesenchymal stem cells and clinical experience. J Intern Med. 262(5):509-25; 2007.
Li, X. et al. Expression of interleukin-12 by adipose-derived mesenchymal stem cells for treatment of lung adenocarcinoma. Thorac Cancer. 6(1):80-4; 2015.
Martinez-Quintanilla, et al. Therapeutic efficacy and fate of biomodal engineered stem cells in malignant brain tumors. Stem Cells 31(8):1706-1714 (2013).
Nakamizo, A. et al. Human bone marrow-derived mesenchymal stem cells in the treatment of gliomas. Cancer Res. 65(8):3307-18; 2005.

(Continued)

*Primary Examiner* — Elly-Gerald Stoica
(74) *Attorney, Agent, or Firm* — Wilson Sonsini Goodrich & Rosati

(57) ABSTRACT

Cancer is a complex group of diseases involving abnormal cell growth with the potential to invade or spread to other parts of the body. Described herein are compositions and methods for the treatment of cancer.

8 Claims, 20 Drawing Sheets

Specification includes a Sequence Listing.

(56) References Cited

OTHER PUBLICATIONS

PCT/US2017/036332 International Search Report and Written Opinion dated Oct. 30, 2017.
Ramos, C.A. et al. An inducible caspase 9 suicide gene to improve the safety of mesenchymal stromal cell therapies. Stem Cells. 28(6):1107-15; 2010.
Ryan, J.M. Mesenchymal stem cells avoid allogeneic rejection. J Inflamm (Lond). 26;2:8; 2005.
Sage et al. Systemic but not topical TRAIL-expressing mesenchymal stem cells reduce tumour growth in malignant mesothelioma. Thorax 69:638-647 (2014).
Sasportas, L.S., et al. Assessment of therapeutic efficacy and fate of engineered human mesenchymal stem cells for cancer therapy. Proc Natl Acad Sci U S A. Mar. 24, 2009;106(12):4822-7.
Seo, S.H. et al. The effects of mesenchymal stem cells injected via different routes on modified IL-12-mediated antitumor activity. Gene Ther. 18(5):488-95; 2011.
Shah. Mesenchymal Stem Cells Engineered For Cancer Therapy. Adv Drug Deliv Rev 64(8):739-748 (2012).
Stephan, SB et al. Biopolymer implants enhance the efficacy of adoptive T-cell therapy. Nat Biotechnol. 33(1):97-101; 2015.
Sundelin, et al. Effects of cisplatin, a-interferon, and 13-cis retinoic acid on the expression of Fas (CD95), intercellular adhesion molecule-1 (ICAM-1), and epidermal growth factor receptor (EGFR) in oral cancer cell lines. Journal Oral Pathol. Med. 36:177-183 (2007).
Talwadekar, M.D. Placenta-derived mesenchymal stem cells possess better immunoregulatory properties compared to their cord-derived counterparts—a paired sample study. Sci Rep. 5:15784; 2015.
Trounson, A. et al. Stem Cell Therapies in Clinical Trials: Progress and Challenges. Cell Stem Cell. 17(1):11-22; 2015.
U.S. Appl. No. 15/616,393 Final Office Action dated Jul. 10, 2018.
U.S. Appl. No. 15/616,393 Non-Final Office Action dated Jan. 12, 2018.
Wang, G.X. et al. Mesenchymal stem cells modified to express interferon-$\beta$ inhibit the growth of prostate cancer in a mouse model. J Int Med Res. 40(1):317-27; 2012.
You Q. Effect of targeted ovarian cancer therapy using amniotic fluid mesenchymal stem cells transfected with enhanced green fluorescent protein-human interleukin-2 in vivo. Mol Med Rep. 12(4):4859-66; 2015.
Bo-Rim et al., Suppression of the growth of human colorectal cancer cells by therapeutic stem cells expressing cytosine deaminase and interferon-[beta] via their tumor-tropic effect in cellular and xenograft mouse models. Molecular Oncology 7(3): 543-554 (2013).
European Patent Application No. 17810929.4 Supplementary Search Report dated Jan. 29, 2020.
Grisendi et al., Adipose-Derived Mesenchymal Stem Cells as Stable Source of Tumor Necrosis Factor-Related Apoptosis-Inducing Ligand Delivery for Cancer Therapy. Cancer Research 70(9): 3718-3729 (2010).
Quintarelli et al., Co-expression of cytokine and suicide genes to enhance the activity and safety of tumor-specific cytotoxic T lymphocytes. Blood 110(8): 2793-2802 (2007).
Zhen-Wu et al., A new method for linking two subunits gene p35 and p40 of IL-12. Journal of Jilin University (Medicine Edition) 35(2): 309-313 (2009).

SEQUENCE LISTING

<160> NUMBER OF SEQ ID NOS: 13

<210> SEQ ID NO 1
<211> LENGTH: 536
<212> TYPE: PRT
<213> ORGANISM: Homo sapiens

<400> SEQUENCE: 1

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240
```

-continued

```
Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Val Pro Gly Val Gly Val Pro Gly
                325                 330                 335

Val Gly Ala Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser
    530                 535

<210> SEQ ID NO 2
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Thr Phe Pro Lys Arg Gly Gln Thr Cys Val Val His Tyr Thr Gly Met
1               5                   10                  15

Leu Glu Asp Gly Lys Lys Val Asp Ser Ser Arg Asp Arg Asn Lys Pro
            20                  25                  30

Phe Lys Phe Met Leu Gly Lys Gln Glu Val Ile Arg Gly Trp Glu Glu
        35                  40                  45

Gly Val Ala Gln Met Ser Val Gly Gln Arg Ala Lys Leu Thr Ile Ser
    50                  55                  60
```

-continued

```
Pro Asp Tyr Ala Tyr Gly Ala Thr Gly His Pro Gly Ile Ile Pro Pro
 65                  70                  75                  80

His Ala Thr Leu Val Phe Asp Val Glu Leu Leu Lys Leu Glu Ser Gly
                 85                  90                  95

Gly Gly Ser Gly Val Asp Gly Phe Gly Asp Val Gly Ala Leu Glu Ser
            100                 105                 110

Leu Arg Gly Asn Ala Asp Leu Ala Tyr Ile Leu Ser Met Glu Pro Cys
        115                 120                 125

Gly His Cys Leu Ile Ile Asn Asn Val Asn Phe Cys Arg Glu Ser Gly
    130                 135                 140

Leu Arg Thr Arg Thr Gly Ser Asn Ile Asp Cys Glu Lys Leu Arg Arg
145                 150                 155                 160

Arg Phe Ser Ser Leu His Phe Met Val Glu Val Lys Gly Asp Leu Thr
                165                 170                 175

Ala Lys Lys Met Val Leu Ala Leu Leu Glu Leu Ala Gln Gln Asp His
            180                 185                 190

Gly Ala Leu Asp Cys Cys Val Val Val Ile Leu Ser His Gly Cys Gln
        195                 200                 205

Ala Ser His Leu Gln Phe Pro Gly Ala Val Tyr Gly Thr Asp Gly Cys
    210                 215                 220

Pro Val Ser Val Glu Lys Ile Val Asn Ile Phe Asn Gly Thr Ser Cys
225                 230                 235                 240

Pro Ser Leu Gly Gly Lys Pro Lys Leu Phe Phe Ile Gln Ala Cys Gly
                245                 250                 255

Gly Glu Gln Lys Asp His Gly Phe Glu Val Ala Ser Thr Ser Pro Glu
            260                 265                 270

Asp Glu Ser Pro Gly Ser Asn Pro Glu Pro Asp Ala Thr Pro Phe Gln
        275                 280                 285

Glu Gly Leu Arg Thr Phe Asp Gln Leu Asp Ala Ile Ser Ser Leu Pro
    290                 295                 300

Thr Pro Ser Asp Ile Phe Val Ser Tyr Ser Thr Phe Pro Gly Phe Val
305                 310                 315                 320

Ser Trp Arg Asp Pro Lys Ser Gly Ser Trp Tyr Val Glu Thr Leu Asp
                325                 330                 335

Asp Ile Phe Glu Gln Trp Ala His Ser Glu Asp Leu Gln Ser Leu Leu
            340                 345                 350

Leu Arg Val Ala Asn Ala Val Ser Val Lys Gly Ile Tyr Lys Gln Met
        355                 360                 365

Pro Gly Cys Phe Asn Phe Leu Arg Lys Lys Leu Phe Phe Lys Thr Ser
    370                 375                 380

Val Asp Tyr Pro Tyr Asp Val Pro Asp Tyr Ala Leu Asp
385                 390                 395

<210> SEQ ID NO 3
<211> LENGTH: 413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Leu Glu Gly Val Gln Val Glu Thr Ile Ser Pro Gly Asp Gly Arg
  1               5                  10                  15

Thr Phe Pro Lys Arg Gly Gln Thr Cys Val Val His Tyr Thr Gly Met
                 20                  25                  30
```

-continued

Leu Glu Asp Gly Lys Lys Val Asp Ser Ser Arg Asp Arg Asn Lys Pro
             35                  40                  45

Phe Lys Phe Met Leu Gly Lys Gln Glu Val Ile Arg Gly Trp Glu Glu
 50                  55                  60

Gly Val Ala Gln Met Ser Val Gly Gln Arg Ala Lys Leu Thr Ile Ser
 65                  70                  75                  80

Pro Asp Tyr Ala Tyr Gly Ala Thr Gly His Pro Gly Ile Ile Pro Pro
                 85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
            115                 120                 125

Leu Arg Gly Asn Ala Asp Leu Ala Tyr Ile Leu Ser Met Glu Pro Cys
130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Val Ile Leu Ser His Gly Cys Gln
210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
            340                 345                 350

Asp Ile Phe Glu Gln Trp Ala His Ser Glu Asp Leu Gln Ser Leu Leu
        355                 360                 365

Leu Arg Val Ala Asn Ala Val Ser Val Lys Gly Ile Tyr Lys Gln Met
370                 375                 380

Pro Gly Cys Phe Asn Phe Leu Arg Lys Lys Leu Phe Phe Lys Thr Ser
385                 390                 395                 400

Val Asp Tyr Pro Tyr Asp Val Pro Asp Tyr Ala Leu Asp
                405                 410

<210> SEQ ID NO 4
<211> LENGTH: 328
<212> TYPE: PRT
<213> ORGANISM: Homo sapiens

<400> SEQUENCE: 4

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 5
<211> LENGTH: 253
<212> TYPE: PRT
<213> ORGANISM: Homo sapiens

<400> SEQUENCE: 5

Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
            20                  25                  30
```

-continued

```
Leu Ser Met Cys Pro Ala Arg Ser Leu Leu Val Ala Thr Leu Val
         35                  40                  45

Leu Leu Asp His Leu Ser Leu Ala Arg Asn Leu Pro Val Ala Thr Pro
 50                  55                  60

Asp Pro Gly Met Phe Pro Cys Leu His His Ser Gln Asn Leu Leu Arg
 65                  70                  75                  80

Ala Val Ser Asn Met Leu Gln Lys Ala Arg Gln Thr Leu Glu Phe Tyr
                 85                  90                  95

Pro Cys Thr Ser Glu Glu Ile Asp His Glu Asp Ile Thr Lys Asp Lys
                100                 105                 110

Thr Ser Thr Val Glu Ala Cys Leu Pro Leu Glu Leu Thr Lys Asn Glu
            115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 6
<211> LENGTH: 285
<212> TYPE: PRT
<213> ORGANISM: Homo sapiens

<400> SEQUENCE: 6

Gly Ser Gly Gly Phe Gly Asp Val Gly Ala Leu Glu Ser Leu Arg Gly
1               5                   10                  15

Asn Ala Asp Leu Ala Tyr Ile Leu Ser Met Glu Pro Cys Gly His Cys
                20                  25                  30

Leu Ile Ile Asn Asn Val Asn Phe Cys Arg Glu Ser Gly Leu Arg Thr
            35                  40                  45

Arg Thr Gly Ser Asn Ile Asp Cys Glu Lys Leu Arg Arg Arg Phe Ser
        50                  55                  60

Ser Leu His Phe Met Val Glu Val Lys Gly Asp Leu Thr Ala Lys Lys
65                  70                  75                  80

Met Val Leu Ala Leu Leu Glu Leu Ala Gln Gln Asp His Gly Ala Leu
                85                  90                  95

Asp Cys Cys Val Val Val Ile Leu Ser His Gly Cys Gln Ala Ser His
            100                 105                 110

Leu Gln Phe Pro Gly Ala Val Tyr Gly Thr Asp Gly Cys Pro Val Ser
        115                 120                 125

Val Glu Lys Ile Val Asn Ile Phe Asn Gly Thr Ser Cys Pro Ser Leu
    130                 135                 140

Gly Gly Lys Pro Lys Leu Phe Phe Ile Gln Ala Cys Gly Gly Glu Gln
145                 150                 155                 160
```

```
Lys Asp His Gly Phe Glu Val Ala Ser Thr Ser Pro Glu Asp Glu Ser
                165                 170                 175
Pro Gly Ser Asn Pro Glu Pro Asp Ala Thr Pro Phe Gln Glu Gly Leu
            180                 185                 190
Arg Thr Phe Asp Gln Leu Asp Ala Ile Ser Ser Leu Pro Thr Pro Ser
        195                 200                 205
Asp Ile Phe Val Ser Tyr Ser Thr Phe Pro Gly Phe Val Ser Trp Arg
    210                 215                 220
Asp Pro Lys Ser Gly Ser Trp Tyr Val Glu Thr Leu Asp Asp Ile Phe
225                 230                 235                 240
Glu Gln Trp Ala His Ser Glu Asp Leu Gln Ser Leu Leu Arg Val
                245                 250                 255
Ala Asn Ala Val Ser Val Lys Gly Ile Tyr Lys Gln Met Pro Gly Cys
                260                 265                 270
Phe Asn Phe Leu Arg Lys Lys Leu Phe Phe Lys Thr Ser
                275                 280                 285
```

```
<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Phe Leu Ile Asp
1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Asp Pro Asp Met Ile Arg Tyr Ile Asp Glu Phe Gly Gln Thr
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Gly Gly Gly Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Gly Gly
1               5
```

```
<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Ala Ala Ala Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5
```

COMPOSITIONS AND METHODS FOR REDUCING TUMOR CELL GROWTH AT A SITE OF SOLID TUMOR EXCISION

CROSS-REFERENCE

This application is a continuation of U.S. patent application Ser. No. 15/616,393 filed Jun. 7, 2017, which claims the benefit of U.S. Provisional Application No. 62/347,005 filed on Jun. 7, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 19, 2018, is named 49537-701_301_SL.txt and is 21,238 bytes in size.

BACKGROUND

Cancer is a complex group of diseases involving abnormal cell growth with the potential to invade or spread to other parts of the body. Millions of new cases of cancer occur globally each year. There are many risk factors of cancer, including obesity, poor diet, lack of physical activity, tobacco use, alcohol use, and genetic and hormonal factors. Cancer is associated with cell growth and division absent the proper signals, continuous growth and division even given contrary signals, avoidance of programmed cell death, limitless number of cell divisions, promoting blood vessel construction, and invasion of tissue and formation of metastases. There is numerous research dedicated to improve understanding of the disease and to identify and create new treatments.

SUMMARY

Provided herein, in certain embodiments, are methods of targeting cancer at a site of tumor excision, comprising: introducing to the site of tumor excision a composition comprising an anti-tumor agent and an apoptotic agent, wherein the anti-tumor agent induces an immune response; and administering an exogenous signal to clear the composition from the site of tumor excision. In certain embodiments, the composition is administered immediately after tumor excision. In certain embodiments, the cancer is at least one of breast cancer, colon cancer, rectal cancer, lung cancer, ovarian cancer, prostate cancer, skin cancer, brain cancer, bladder cancer, endometrial cancer, kidney cancer, pancreatic cancer, thyroid cancer, mesothelioma, and melanoma. In certain embodiments, the cancer is mesothelioma. In certain embodiments, the anti-tumor agent is expressed in a stem cell. In certain embodiments, the stem cell is a human-derived stem cell. In certain embodiments, the stem cell is a mesenchymal stem cell. In certain embodiments, the mesenchymal stem cell is derived from human placenta or bone marrow. In certain embodiments, the anti-tumor agent has cytokine activity. In certain embodiments, the anti-tumor agent comprises a fusion of two or more cytokines. In certain embodiments, the anti-tumor agent comprises an interleukin. In certain embodiments, the interleukin comprises at least one interleukin selected from a list consisting of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, and interleukin-36. In certain embodiments, the interleukin comprises interleukin-12. In certain embodiments, the interleukin-12 comprises a fusion of IL-12p40 and IL-12p35. In certain embodiments, the apoptotic agent is induced by the exogenous signal. In certain embodiments, the apoptotic agent has caspase activity. In certain embodiments, the caspase comprises at least one caspase selected from a list consisting of caspase-1, caspase-2, caspase-3, caspase-4, caspase-5, caspase-6, caspase-7, caspase-8, caspase-9, caspase-10, caspase-13, and caspase-14. In certain embodiments, the caspase is caspase-9. In certain embodiments, the exogenous signal is administered systemically. In certain embodiments, the exogenous signal induces multimerization of the apoptotic agent.

Provided herein, in certain embodiments, are compositions comprising at least one genetically modified stem cell, said stem cell is modified to express an anti-tumor agent and an apoptotic agent. In some embodiments, the stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the anti-tumor agent is encoded by a nucleic acid. In some embodiments, the anti-tumor agent comprises a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one of interferon-alpha, interferon-beta, interferon-epsilon, interferon-kappa, interferon-omega, or interferon-gamma. In some embodiments, the cytokine comprises transforming growth factor beta. In some embodiments, the anti-tumor agent comprises a nucleic acid encoding a p53 protein. In some embodiments, the anti-tumor agent is a virus. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor.

Provided herein, in certain embodiments, are methods of inducing a subject's immune system to target cancer cells comprising introducing into the subject at least one genetically modified stem cell, wherein said stem cell is modified to express an anti-tumor agent. In some embodiments, the at least one genetically modified stem cell is introduced to the subject by injection. In some embodiments, the genetically modified stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the anti-tumor agent is encoded by a nucleic acid. In some embodiments, the nucleic acid encodes a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is a virus. In some embodiments, the genetically modified stem cell further comprises an apoptotic agent. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor.

Provided herein, in certain embodiments, are methods of introducing at least one genetically modified stem cell comprising nucleic acid encoding an anti-tumor agent and an apoptotic agent to a subject who has undergone tumor removal surgery. In some embodiments, the cancer is mesothelioma. In some embodiments, the mesothelioma is malignant pleural mesothelioma. In some embodiments, the at least one genetically modified stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the anti-tumor agent is encoded by a nucleic acid. In some embodiments, the nucleic acid is a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one of interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is a virus. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor. In some embodiments, the surgery removes a tumor. In some embodiments, the surgery is a pleurectomy or a decortication. In some embodiments, the at least one genetically modified stem cell is introduced to the subject by injection. In some embodiments, the at least one genetically modified stem cell is introduced to the subject before surgery, concurrent with surgery, one week post-surgery, two weeks post-surgery, one month post-surgery, two months post-surgery, three months post-surgery, four months post-surgery, five months post-surgery, one year post-surgery, two years post-surgery, three years post-surgery, four years post-surgery, or five years post-surgery.

Provided herein, in certain embodiments, are methods of targeting cancer cells in a subject to alleviate the symptoms of cancer comprising introducing to the subject at least one genetically modified stem cell, wherein said stem cell is modified to express an anti-tumor agent and an apoptotic agent, and wherein the at least one genetically modified stem cell is introduced subsequent to tumor removal. In some embodiments, the cancer is mesothelioma. In some embodiments, the mesothelioma is malignant pleural mesothelioma. In some embodiments, the genetically modified stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the anti-tumor agent is encoded by a nucleic acid. In some embodiments, the nucleic acid encodes a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one of interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is a virus. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor. In some embodiments, surgery removes a tumor. In some embodiments, the surgery is a pleurectomy or a decortication. In some embodiments, the genetically modified stem cells are introduced through injection 1 month, 2 months, 3 months, 4 months, 5 months, 6 months, 7 months, 8 months, 9 months, 10 months, 11 months, 12 months, 13 months, 14 months, or 15 months after surgery.

Provided herein, in certain embodiments, are methods to target cancer comprising introducing to a subject in need thereof at least one genetically modified stem cell, wherein said stem cell is modified to express an anti-tumor agent and an apoptotic agent. In some embodiments, the cancer is mesothelioma. In some embodiments, the mesothelioma is malignant pleural mesothelioma. In some embodiments, the anti-tumor agent is encoded by a nucleic acid. In some embodiments, the nucleic acid is a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the cytokine is an interferon. In some embodiments, the interferon comprises at least one of interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is transformed into a stem cell. In some embodiments, the stem cell is a genetically modified stem cell. In some embodiments, the genetically modified stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor.

Provided herein, in certain embodiments, are methods of transforming at least one stem cell into at least one genetically modified stem cell comprising transforming the stem cell with an anti-tumor agent and an apoptotic agent. In some embodiments, the stem cell is transformed with a virus. In some embodiments, the virus is at least one of adenovirus, lentivirus, and adeno-associated virus. In some embodiments, the at least one genetically modified stem cell is introduced to the subject in need thereof by injection. In some embodiments, the genetically modified stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the anti-tumor agent is encoded by a nucleic acid. In some embodiments, the nucleic acid encodes a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is a virus. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor.

Provided herein, in certain embodiments, are kits comprising: a population of genetically modified stem cells, wherein said stem cells are modified to express an anti-tumor agent and an apoptotic agent, wherein the population of genetically modified stem cells are aliquoted in a relevant pharmaceutical dose for administration. In some embodiments, the stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the population of genetically modified stem cells are frozen. In some embodiments, the population of genetically modified stem cells are autologous. In some embodiments, the population of genetically modified stem cells are allogeneic. In some embodiments, the population of genetically modified stem cells comprises about 500,000 cells/kg to about 1,000,000 cells/kg. In some embodiments, the anti-tumor agent is encoded by a nucleic acid. In some embodiments, the anti-tumor agent comprises a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one of interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is a virus. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprise apoptosis-inducing factor.

Provided herein, in certain embodiments, are methods of measuring the therapeutic potential of at least one genetically modified stem cell comprising an anti-tumor agent and an apoptotic agent in the treatment of cancer. In some embodiments, the cancer is mesothelioma. In some embodiments, the mesothelioma is malignant pleural mesothelioma. In some embodiments, the genetically modified stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the anti-tumor agent is encoded by a nucleic acid. In some embodiments, the nucleic acid encodes a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one of interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is a virus. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor. In some embodiments, the genetically modified stem cells are introduced through injection 1 month, 2 months, 3 months, 4 months, 5 months, 6 months, 7 months, 8 months, 9 months, 10 months, 11 months, 12 months, 13 months, 14 months, or 15 months after surgery. In some embodiments, the therapeutic potential is measured by the reduction or elimination of symptoms associated with cancer. In some embodiments, the symptoms associated with cancer comprise at least one of chest wall pain, pleural effusion, shortness of breath, fatigue, anemia, wheezing, hoarseness, cough, blood in the sputum, coughing blood, abdominal pain, ascites, abdominal mass, problems with bowel function, weight loss, blood clots in the veins, thrombophlebitis, disseminated intravascular coagulation, jaundice, low blood sugar, pleural effusion, pulmonary emboli, and severe ascites.

Provided herein, in certain embodiments, are methods of inhibiting a wound healing response by administering at least one genetically modified stem cell comprising an anti-tumor agent and an apoptotic agent. In some embodiments, the stem cell is a human-derived stem cell. In some embodiments, the human-derived stem cell is a mesenchymal stem cell. In some embodiments, the mesenchymal stem cell is derived from human placenta. In some embodiments, the mesenchymal stem cell is derived from human bone marrow. In some embodiments, the anti-tumor agent is encoded by a nucleic acid. In some embodiments, the anti-tumor agent comprises a cytokine. In some embodiments, the cytokine comprises a fusion of two or more cytokines. In some embodiments, the cytokine is an interleukin. In some embodiments, the interleukin is at least one of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, or interleukin-36. In some embodiments, the interleukin comprises interleukin-12. In some embodiments, the interleukin-12 comprises a fusion of IL-12p40 and IL-12p35. In some embodiments, the interleukin-12 nucleic acid is transformed into the stem cell through an adenovirus. In some embodiments, the cytokine is an interferon. In some embodiments, the interferon comprises at least one of interferon-alpha, interferon-beta, interferon-epsilon, interferon-kappa, interferon-omega, or interferon-gamma. In some embodiments, the cytokine is transforming growth factor beta. In some embodiments, the anti-tumor agent comprises a nucleic acid encoding a p53 protein. In some embodiments, the anti-tumor agent is a virus. In some embodiments, the apoptotic agent is encoded by a nucleic acid. In some embodiments, the nucleic acid encodes an inducible caspase. In some embodiments, the caspase is at least one of caspase-1, caspase-2, caspase-3, caspase-4, caspase-5, caspase-6, caspase-7, caspase-8, caspase-9, caspase-10, caspase-13, or caspase-14. In some embodiments, the caspase is caspase-9. In some embodiments, the caspase-9 nucleic acid is transformed into the stem cell through an adenovirus. In some embodiments, the nucleic acid encodes a cytokine. In some embodiments, the cytokine is a tumor necrosis factor. In some embodiments, the tumor necrosis factor comprises at least one of tumor necrosis factor alpha or tumor necrosis factor beta. In some embodiments, the nucleic acid encodes a flavoprotein. In some embodiments, the flavoprotein comprises apoptosis-inducing factor.

DETAILED DESCRIPTION

Figure 1:
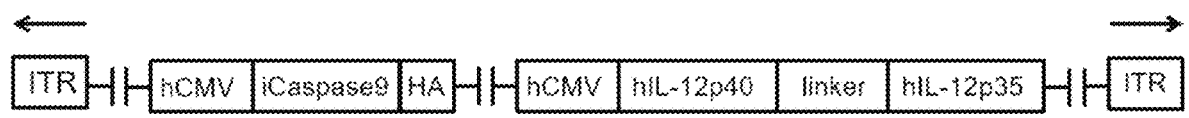
FIG. 1 depicts an adenovirus vector expression cassette comprising human IL-12 and iCasp9 genes (Ad.IL.12.iCasp9).

Cancer is a complex group of diseases involving abnormal cell growth with the potential to invade or spread to other parts of the body. Cancer therapies such as radiation and chemotherapy that target cancer drivers and pathways can be successful. The ability of cancer cells to adapt to these therapies, however, results in disease progression in patients. Immunotherapy, unlike surgery, chemotherapy, or radiation, stimulates the immune system to recognize and kill tumor cells. Cancer cells often avoid detection by the immune system. Cancer immunotherapy directs a patient's immune system to express cancer cell antigens, triggering the body to attack cancer cells.

Disclosed herein are cells such as stem cells that selectively home or migrate to a site of injury, ischemia, or wounding and are engineered to induce an innate immune response at the site. The immune response may be at a site of introduction such as at a tumor excision site. The stem cells are also engineered to be induced, upon receipt of a signal or contacting to a molecule, to activate an apoptotic or "suicide" molecule that triggers cell death so as to control cell proliferation or otherwise clear the cells when desired.

Further described herein are methods and compositions relating to cancer therapies comprising genetically modified stem cells. Often genetically modified stem cells as contemplated herein comprise at least one anti-tumor agent that is immunostimulatory to a host cell, and at least one regulatory agent that allows for modulation of genetically modified stem cell function such by inducing cell death upon a signaling molecule.

Genetically modified stem cells transformed with at least one anti-tumor agent and at least one regulatory agent as described herein are administered to a subject in need thereof. Following administration to a subject in need thereof, genetically modified stem cells often home to a tumor site and preferentially migrate to sites of tissue injury. In some instances, the anti-tumor agent enhances T cell activation, triggering a subject's immune system to clear cancer cells. Cancer therapies as described herein often promote wound clearance and modify the wound site as to create an environment amenable to an immune response rather than a wound healing response. Alternately or in combination, cancer therapies as described herein inhibit proliferation at a wound site.

Additionally, genetically modified stem cells transformed with at least one anti-tumor agent and at least one regulatory agent are administered to a subject in need thereof in combination with surgery. Surgery results in removal of a tumor, but often cancer cells that are difficult to remove or hard to detect remain. In some instances, surgery is unable to remove precancerous cells. In some instances, remaining cancer cells or precancerous cells proliferate and promote tumor formation. Genetically modified stem cells as described herein can be used to treat cancer in combination with surgery. In some instances, genetically modified stem cells are administered prior to, during, or following surgery. Genetically modified stem cells can be administered at a tumor site or systemically. Administration of genetically modified stem cells in combination with surgery can result in clearance of cancer cells or precancerous cells that are unable to be removed by surgery.

Cancer therapies comprising genetically modified stem cells transformed with at least one anti-tumor agent and at least one regulatory agent in some cases are administered to a subject in need thereof in combination with chemotherapy or radiation. In some instances, chemotherapy or radiation promotes return of cancer cells. For example, radiation promotes metastatic behavior of cancer cells such as promoting proliferation. As described herein, administration of genetically modified stem cells can result in inhibition of cell proliferation and cell growth and promotion of an immune response. In some instances, genetically modified stem cells are administered prior to, during, or following chemotherapy or radiation. In some instances, administering genetically modified stem cells in combination with chemotherapy or radiation results in clearance of cancer cells that are unable to be removed by chemotherapy or radiation.

In some cases, cancer progression is monitored following administration of genetically modified stem cells transformed with at least one anti-tumor agent and at least one regulatory agent to a subject in need thereof. Exemplary methods of monitoring cancer progression are measuring at least one of circulating blood cells, tumor size by PET scan, or wound healing.

Often to prevent potential adverse effects or once a tumor size is diminished, an exogenous signal is administered to a subject in need thereof. Provided herein is administration of an exogenous signal to modulate genetically modified stem cell function. An exemplary exogenous signal is a small molecule. Often, an exogenous signal causes cell death in genetically modified stem cells.

Methods and Compositions

Described herein are methods and compositions for delivering a tumor inhibiting signal such as an innate immune signal to a particular site such as a tumor site. In some cases, the delivering comprises transforming a gene or genes encoding the signal into a cell or cells that migrate to a particular site such as a tumor site or a site of tumor excision. Once at the tumor site, methods and compositions as described herein may comprise stimulation of an immune response. In some instances, the immune response results in targeting and killing of cancer cells. Following stimulation of an immune response, methods and compositions as described herein may further comprise regulation or modulation of a biological function such as cell death.

Also described herein are methods and compositions relating to genetically modified stem cells that express at least one anti-tumor agent and at least one regulatory agent. Methods and compositions as described herein promote wound clearance and modify the wound site so as to create an environment amenable to an immune response rather than a wound healing response. Mechanisms that promote wound healing have been shown to promote growth and proliferation of malignant cells. By promoting an immune response rather than a wound healing response, a subject's immune system is stimulated to target and kill cancer cells rather than promote their recovery.

Provided herein are methods and compositions for stimulating an immune response. In some instances, stimulating an immune response results in targeting and killing of cancer cells. An exemplary anti-tumor agent for stimulating an immune response is a cytokine. In some instances, the anti-tumor agent such as a cytokine is immunostimulatory. In some instances, the anti-tumor agent triggers a T cell response.

The use of cytokines often increases efficacy of different cancer treatments by stimulating an immune response. For example, use of cytokines can increase the efficacy of immunotherapy, chemotherapy, radiation, or surgery. Cytokines are molecular messengers that coordinate communication between cells of the immune system. Cytokine signaling is involved in host responses to infection, immune responses, inflammation, trauma, sepsis, cancer, and reproduction. Cytokines are produced by a broad range of cells, including immune cells such as macrophages, B lymphocytes, T lymphocytes, mast cells, endothelial cells, fibroblasts, and various stromal cells. Cytokines directly stimulate immune effector cells and stromal cells at the tumor site and enhance tumor cell recognition by cytotoxic effector cells. Cytokines comprise, by way of non-limiting examples, chemokines, interferons, interleukins, lymphokines, and tumor necrosis factors.

Provided herein are methods and compositions for stimulating an immune response using a cytokine. Cytokines as described herein are immunostimulatory. Cytokines include at least one of a colony stimulating factor (CSF), a transforming growth factor (e.g., transforming growth factor-beta), a tumor necrosis factor (e.g., tumor necrosis alpha), an interferon, and an interleukin. In some cases, the anti-tumor agent is at least one of CSF1, CSF2, and CSF3. In some instances, the anti-tumor agent is p53. In some instances, the anti-tumor agent is an interferon such as interferon-alpha, interferon-beta, interferon-epsilon, interferon-kappa, interferon-omega, and interferon-gamma. Exemplary interleukins are interleukin-1 (IL-1), interleukin-1 alpha (IL-1 alpha), interleukin-1 beta (IL-1 beta), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-16 (IL-16), interleukin-17 (IL-17), interleukin-18 (IL-18), interleukin-19 (IL-19), interleukin-20 (IL-20), interleukin-21 (IL-21), interleukin-22 (IL-22), interleukin-23 (IL-23), interleukin-24 (IL-24), interleukin-25 (IL-25), interleukin-26 (IL-26), interleukin-27 (IL-27), interleukin-28 (IL-28), interleukin-29 (IL-29), interleukin-30 (IL-30), interleukin-31 (IL-31), interleukin-32 (IL-32), interleukin-33 (IL-33), interleukin-34 (IL-34), interleukin-35 (IL-35), or interleukin-36 (IL-36). In some instances, the cytokine comprises a fusion of one or more cytokines or portions thereof. For example, the cytokine comprises a fusion of one or more interleukins.

An exemplary interleukin for use in methods and compositions as described herein is IL-12. IL-12 is composed of a bundle of four alpha helices, forming a heterodimeric structure of proteins IL-12A (p35) and IL-12B (p40). The active heterodimer (referred as p70), and a homodimer of p40 are formed following protein synthesis. In some instances, the IL-12 comprises a fusion of interleukins or portions thereof. In some instances, the IL-12 comprises a fusion of IL-12A and IL-12B. In some instances, a molar ratio of IL-12A to IL-12B is at least or about 0.25:1, 0.5:1, 0.75:1, 1:1, 1:1.25, 1:1.5, 1:1.75, 1:2, 1:3, 1:4, or more than 1:4. In some instances, a molar ratio of IL-12A to IL-12B is at least or about 1:1.

Cytokines can be used to treat cancer. In some cases, an anti-tumor agent such as a cytokine is administered as at least one of a recombinant protein, a vaccine containing an anti-tumor agent, a vector encoding an anti-tumor agent, and an antibody. While such methods and compositions of administration of an anti-tumor agent such as a cytokine induce a response, they may not be satisfactory for targeting cancer sites.

Provided herein are methods and compositions for stimulating an immune response at a particular site. For example, the immune response is stimulated at a tumor site or tumor excision site. In some instances, the immune response is stimulated at a site of wounding. In some instances, cells or pathogens are capable of homing to a particular site and inducing an immune response. Exemplary cells that can home to a particular site are stem cells such as MSCs.

Stem cells as described herein home to a tumor site and elicit an immune response. Stem cells as described herein are nonimmunogenic. Provided herein are stem cells that preferentially migrate to sites of wounding and injury.

Stem cells consistent with the present application can be at least one of embryonic, fetal, and adult stem cells. In some cases, stem cells are embryonic or fetal. In some instances, stem cells are adult. Stem cells may be at least one of pluripotent, multipotent, or oligopotent. Stem cells consistent with the application can originate from many different types of tissue such as, but not limited to, bone marrow, skin (e.g., dermis, epidermis), scalp tissue, muscle, adipose tissue, peripheral blood, foreskin, skeletal muscle, smooth muscle, or others. Stem cells in some instances are derived from neonatal tissue, such as, but not limited to, umbilical cord tissues (e.g., the umbilical cord, cord blood, cord blood vessels), the amnion, the placenta, or other various neonatal tissues (e.g., bone marrow fluid, muscle, adipose tissue, peripheral blood, skin, skeletal muscle etc.).

In some instances, stem cells are derived from neonatal mammalian cells such as, but not limited to fibroblasts, bone marrow-derived mononuclear cells, skeletal muscle cells, adipose cells, peripheral blood mononuclear cells, macrophages, neural stem cells, hepatocytes, keratinocytes, oral keratinocytes, hair follicle dermal cells, gastric epithelial cells, lung epithelial cells, synovial cells, kidney cells, skin epithelial cells or osteoblasts. Sometimes stem cells are derived from adult mammalian cells such as, but are not limited to fibroblasts, bone marrow-derived mononuclear cells, skeletal muscle cells, adipose cells, peripheral blood mononuclear cells, macrophages, neural stem cells, hepatocytes, keratinocytes, oral keratinocytes, hair follicle dermal cells, gastric epithelial cells, lung epithelial cells, synovial cells, kidney cells, skin epithelial cells or osteoblasts.

Stem cells in some cases are autologous, meaning derived from a subject's own cells. Alternately, stem cells are allogeneic, meaning derived from another subject with a similar tissue type. In some instances, stem cells are tailored to the patient. In some instances, stem cells are compatible with local tissue.

Stem cells in some cases are non-human. Non-limiting examples of non-human animals include a non-human primate, a livestock animal, a domestic pet, and a laboratory animal. Exemplary non-human stem cells are mouse, rat, equine, sheep, primate (e.g., chimpanzee, baboon, gorilla, orangutan, monkey), dog, cat, pig, donkey, rabbit, or any other non-human animal.

Mesenchymal stem cells (MSCs) are exemplary stem cells consistent with the disclosure. MSCs serve as a therapeutic agent due to their tumor-homing properties and ability to selectively migrate to sites of injury, ischemia, and tumor microenvironments. Tumors secrete inflammatory molecules such as chemokines, cytokines, and growth factors that recruit MSCs to the site of a tumor. MSCs have been demonstrated to home to inflammatory molecules such as stromal cell derived factor 1-alpha and vascular endothelial growth factor secreted by tumors. Once at the site of the tumor, sometimes MSCs engraft in the tumor stroma. Solid tumor growth and invasion create an environment similar to wound healing, which can also induce MSCs to migrate to sites of wounding.

In some instances, stem cells consistent with the disclosure herein such as MSCs or other stem cells are isolated from at least one of brain, liver, kidney, lung, bone marrow, muscle, thymus, pancreas, skin, adipose tissue, fetal tissues, umbilical cord, Wharton's jelly, and placenta. In some cases, the MSCs are derived from placenta. In some instances, the MSCs are derived from bone-marrow. Alternately, MSCs are derived from adipose tissue. In some instances, MSCs are derived from umbilical cord blood. Exemplary cell surface markers for MSCs are CD13, CD29, CD49e, CD54, CD90, but not CD14, CD31, CD34, CD45, and CD49d. In some cases, bone-marrow derived MSCs differentiate into osteocytes and chondrocytes.

While stem cells, such as MSCs, migrate to cancer cells, there is a need to regulate stem cells so that they perform their intended function. Stem cells such as MSCs are immunosuppressive due to their ability to secrete soluble mediators with immunomodulatory properties (e.g., IL-10, prostaglandin E2). In some cases, immunosuppressive effects of stem cells promote tumor progression. Stem cells also promote undifferentiated wound growth by proliferating in response to growth factors and inflammatory molecules released at sites of tissue injury. Stem cells as described herein may be further modified so as to regulate their ability to promote tumor progression and undifferentiated wound growth.

Described herein are stem cells transformed with at least one agent that modulates stem cell function. As disclosed herein, stem cells are modified to express a regulatory agent to be receptive to modulation in response to an exogenous signal. In some instances, an exogenous signal is at least one of a small molecule, an antibody, a nucleic acid encoding an antibody, an antigen binding fragment, a RNA interfering agent, a peptide, a peptidomimetic, a synthetic ligand, and an aptamer. An exogenous signal in some cases is at least one of heat shock, hypoxia, nutrient deficiency, a metal ion, and a steroid.

Exemplary stem cell functions that are regulated are cell death, cell growth, cell proliferation, and cell migration. In some instances, a regulatory agent modulates cell death. Described herein are agents that can be turned on and off. In some instances, genetically modified stem cells are eliminated by triggering a regulatory agent to cause cell death once the genetically modified stem cells have targeted a tumor site and induced an immune response.

An exemplary exogenous signal induces dimerization and subsequent cell death. In some instances, a chimeric protein of a drug binding domain is fused in frame with a component of a cell death pathway to allow conditional dimerization and cell death of transformed cells after administration of a small molecule. Alternately or in combination, a drug binding domain is fused in frame with a component of a proliferative pathway, a migratory pathway, or cell growth pathway. Sometimes a small molecule dimerizes proteins such as FK506-binding protein (FKBP), calcineurin A, cyclophilin, FKBP-rapamycin binding domain of FKPB, B subunit of bacterial DNA gyrase, dihydrofolate reductase, or combinations thereof. In some instances, a small molecule causes heteromerization. In some instances, a small molecule causes homerization. In some instances, a small molecule causes multimerization. In some cases, a small molecule causes trimerization. A small molecule in some cases binds at a domain of a protein and tethers proteins together. Exemplary small molecules are FK1012, FK506, FK506-CsA, FKCsA, rapamycin, coumermycin, gibberellin, HaXS, methotrexate, AP20187, and AP1903. In some instances, a small molecule is AP1903.

An exogenous signal can result in subsequent cell death via alternative mechanisms. In some instances, cell death is induced metabolically. For example, cell death is induced using a gene-directed enzyme prodrug, wherein a nontoxic compound is converted to a toxic compound that results in subsequent cell death. Exemplary proteins that can convert a nontoxic compound to a toxic compound include, but are not limited to, herpes simplex virus thymidine kinase (HSV-TK) and cytosine deaminse (CD). HSV-TK can phosphorylate nucleoside analogs such as ganciclovir or acyclovir that then incorporate into DNA and lead to chain termination and cell death.

In some instances, cell death is induced in an antibody mediated mechanism. In some cases, an exogenous signal causes complement/antibody dependent cell death. Exemplary complement/antibody dependent cell death targets are CD20, RQR8, c-myc, and EGFR. In some instances, cell death is induced using an antibody directed to a surface marker unique to stem cells such as MSCs.

An exemplary regulatory agent is a cell death agent. Exemplary cell death agents include, by way of non-limiting example, caspase, tumor necrosis factor, flavoprotein, thymidine kinase, cytosine deaminase, purine nucleoside phosphorylase, cytochrome p450 enzymes, carboxypeptidase, carboxylesterase, nitroreductase, horse radish peroxidase, guanine ribosyltransferase, glycosidase enzymes, methionine-α-γ-lyase, and thymidine phosphorylase. In some instances, the cell death agent is an apoptotic agent. In some instances, the apoptotic agent eliminates cells by inducing apoptosis.

Often an apoptotic agent is a caspase such as, by way of non-limiting example, caspase-1, caspase-2, caspase-3, caspase-4, caspase-5, caspase-6, caspase-7, caspase-8, caspase-9, caspase-10, caspase-13, and caspase-14. Often the anti-tumor agent is caspase 9. In some instances, the apoptotic agent is a tumor necrosis factor such as tumor necrosis factor alpha or tumor necrosis factor beta. The apoptotic agent can be a flavoprotein (e.g., apoptosis-inducing factor).

Provided herein are methods and compositions relating to genetically modified stem cells transformed with at least one anti-tumor agent and at least one regulatory agent. In some instances, stem cells are modified using a vector. In some instances, the vector is at least one of lentivirus, oncoretrovirus, expression plasmid, adenovirus, adeno-associated virus, herpes simplex virus, transposon, vaccinia virus, human papilloma virus, Simian immunodeficiency virus, HTLV, human foamy virus, spumaviruses, mammalian type B retrovirus, mammalian type C retrovirus, avian type C retrovirus, mammalian type D retrovirus, and HTLV/BLV type retrovirus. An adenovirus from one of the Aviadenovirus, Mastadenovirus, Atadenovirus, Ichtadenovirus, and Siadenovirus genera of the family Adenoviridae may be used. In some instances, a serotype found within the five genera of Adenoviridae is used.

An exemplary adenovirus vector containing human IL-12 and iCasp9 is seen in FIG. 1. In some instances, a viral vector is generated by insertion of an expression cassette. The expression cassette can be inserted into a vector using techniques known in the art. In some instances, the vector is modified using a CRISPR/Cas9 system.

In some instances, the expression cassette comprises at least one polynucleotide encoding for a polypeptide. In some instances, the at least one polynucleotide encodes for Caspase 9. In some instances, the at least one polynucleotide encodes for a cytokine. In some instances, the cytokine comprises IL-12. In some instances, the cytokine comprises a fusion of two or more cytokines. In some instances, the cytokine comprises a fusion of IL-12p40 and IL-12p35. For example, the at least one polynucleotide encodes IL-12p35. In some instances, the at least one polynucleotide encodes IL-12p40.

Provided herein are genetically modified stem cells, wherein a fusion polypeptide such as one comprising IL-12 is connected by a linker. The linker may connect a portion or fragment of a cytokine in proximity as to maintain a functional protein. In some instances, the functional protein is a functional equivalent of an assembled IL-12p35 and IL-12p40 heterodimer. In some instances, the linker is a flexible linker, a rigid linker, or a cleavable linker. Exemplary linkers include, but are not limited to, elastin, a GS linker, a $(Gly)_8$ linker (SEQ ID NO: 9), a $(Gly)_6$ linker (SEQ ID NO: 10), a $(GGGGS)_3$ linker (SEQ ID NO: 11), a (EAAAK)n linker (SEQ ID NO: 12), and a (XP)n linker. In some instances, the at least one polynucleotide encodes for a tag. In some instances, the tag is hemagglutinin (HA), FLAG, glutathione S transferase (GST), or hexa-his (SEQ ID NO: 13). In some instances, the at least one polynucleotide sequence encodes for one or more inverted terminal repeats (ITRs) for adenoviral replication.

Provided herein are genetically modified stem cells, wherein an expression or activity of a polypeptide such as IL-12 is under a control of a promoter. In some instances, the promoter allows for the polypeptide to induce an immune response. In some instances, the promoter allows for the polypeptide to induce an immune response at a specific site. For example, the promoter is active at a tumor site or a wound healing site. By way of non-limiting example, a promoter is at least one of cytomegalovirus (CMV), CAG, H1, U6, Synapsin, UBC, EF1-alpha, ALB(1.4), ApoE/AAT1, CaMKII, ELA1, Enh358MCK, cTNT, GFAP, MBP, SST, TBG, alpha-MHC, hRPE, mIP1, tMCK, VEGF, Rec-A, Egr-1, and WAF-1. Often a promoter is CMV. An exemplary promoter is human. Alternately, a promoter is non-human such as mouse, rat, equine, sheep, primate (e.g., chimpanzee, baboon, gorilla, orangutan, monkey), dog, cat, pig, donkey, rabbit, or any other non-human animal.

In some cases, a promoter is chosen so that an expression cassette is constitutively active. Alternately, a promoter is chosen so that an expression cassette is expressed in a tissue specific manner. A promoter in some instances is responsive to at least one of hypoxia, nutrient deficiency, and radiation.

Provided herein are methods and compositions comprising genetically modified stem cells, wherein the stem cells are characterized prior to use. In some instances, the genetically modified stem cells are sorted to identify stem cells such as MSCs. Exemplary methods of sorting are flow cytometry and magnetic sorting. Often genetically modified stem cells, such as MSCs, retain their natural secretomes, surface marker phenotypes, and cellular differentiation capabilities. In some cases, secretomes of stem cells are measured by high-throughput multiplex bead array.

In some instances, the MSCs are identified or characterized as MSCs by surface markers. Exemplary surface markers for identification of MSCs include, but are not limited to, CD34, CD45, CD11b, CD14, CD79 alpha, CD19 alpha, HLA Class II, CD73 (5'-Nucleotidase), CD90 (Thy120), CD105 (Endoglin), STRO-1, CD271 (NGF R), CD200, Ganglioside GD2, Frizzled-9, and Tissue Non-specific Alkaline Phosphatase (TNAP). In some instances, expression is measured by at least one of flow cytometry, immunofluorescence, immunocytochemistry, Western blot, protein array, or quantitative PCR. In some instances, the MSCs are identified or characterized by low expression of at least one of CD34, CD11b, CD19, CD45, and HLA-DR and high expression of at least one of CD90, CD73, and CD105. In some instances, expression of CD34, CD11b, CD19, CD45, or HLA-DR in a population of MSCs is at most 1%, at most 2%, at most 3%, at most 4%, at most 5%, at most 6%, at most 7%, at most 8%, at most 9%, at most 10%, at most 11%, at most 12%, at most 13%, at most 14%, at most 15%, at most 16%, at most 17%, at most 18%, at most 19%, or at most 20%. In some instances expression of CD90 in a population of MSCs is at least 85%, at least 90%, at least 95%, at least 97.5%, or at least 99%. In some instances expression of CD90 in a population of MSCs is about 85%, about 90%, about 95%, about 97.5%, or about 99%. In some instances expression of CD73 in a population of MSCs is at least 85%, at least 90%, at least 95%, at least 97.5%, or at least 99%. In some instances expression of CD73 in a population of MSCs is about 85%, about 90%, about 95%, about 97.5%, or about 99%. In some instances expression of CD105 is at least 85%, at least 90%, at least 95%, at least 97.5%, or at least 99%. In some instances expression of CD105 in a population of MSCs is about 85%, about 90%, about 95%, about 9'7.5%, or about 99%.

In some instances, the MSCs are identified or characterized as MSCs by differentiation assays. For example, MSCs are identified by their ability to differentiate into at least one of chondrocytes, osteocytes, and adipocytes.

Provided herein are genetically modified stem cells to express an anti-tumor agent and an apoptotic agent. In some instances, the anti-tumor agent comprises a cytokine such as IL-12 for inducing an immune response. In some instances, the immune response results from secretion of one or more cytokines at a particular site such as a tumor site or tumor excision site. In some instances, the genetically modified stem cells secrete IL-12. For example, MSCs expressing IL-12 iCasp9 result in an increase in secretion of human IL-12 (IL-12p70). In some instances, MSCs transformed with IL-12 iCasp9 using adenovirus show a substantial higher fold secretion of IL-12p70. In some instances, an amount of IL-12p70 that is secreted from MSCs is at least 500000, at least 750000, at least 1000000, at least 2000000, at least 3000000, at least 4000000, at least 5000000, at least 6000000, at least 7000000, at least 8000000, at least 9000000, at least 10000000, at least 110000000, at least 12000000, at least 13000000, at least 14000000, at least 15000000, or more than 15000000 moles as compared to MSCs not expressing IL-12p70. In some instances, an amount of IL-12p70 that is secreted from MSCs is in a range of about 500000 to 1000000, 500000 to 2000000, 500000 to 3000000, 500000 to 4000000, 500000 to 5000000, 500000 to 6000000, 500000 to 7000000, 500000 to 8000000, 500000 to 9000000, 500000 to 10000000, 1000000 to 2000000, 1000000 to 3000000, 1000000 to 4000000, 1000000 to 5000000, 1000000 to 6000000, 1000000 to 7000000, 1000000 to 8000000, 1000000 to 9000000, 1000000 to 10000000, 2000000 to 3000000, 2000000 to 4000000, 2000000 to 5000000, 2000000 to 6000000, 2000000 to 7000000, 2000000 to 8000000, 2000000 to 9000000, 2000000 to 10000000, 3000000 to 4000000, 3000000 to 5000000, 3000000 to 6000000, 3000000 to 7000000, 3000000 to 8000000, 3000000 to 9000000, 3000000 to 10000000, 4000000 to 5000000, 4000000 to 6000000, 4000000 to 7000000, 4000000 to 8000000, 4000000 to 9000000, 4000000 to 10000000, 5000000 to 6000000, 5000000 to 7000000, 5000000 to 8000000, 5000000 to 9000000, 5000000 to 10000000, 6000000 to 7000000, 6000000 to 8000000, 6000000 to 9000000, 6000000 to 10000000, 7000000 to 8000000, 7000000 to 9000000, 7000000 to 10000000, 8000000 to 9000000, 8000000 to 10000000, or 9000000 to 10000000 moles as compared to MSCs not expressing IL-12p70.

Provided herein are MSCs transformed using Ad. IL-12 iCasp9 that can induce an immune response, wherein the immune response comprises activation of T cells. In some instances, genetically modified MSCs promote T cell proliferation.

Provided herein are MSCs transformed using Ad. IL-12 iCasp9 that exhibit enhanced tumor-homing properties. In some instances, MSCs transformed using an expression vector such as Ad. IL-12 iCasp9 selectively migrate to at least one of sites of injury and sites of ischemia. In some instances, MSCs transformed using Ad. IL-12 iCasp9 selectively migrate to sites of the tumor.

Provided herein are stem cells genetically modified to express an anti-tumor agent. In some instances, the anti-tumor agent is IL-12. Often IL-12 is expressed as a single polypeptide. An exemplary human IL-12 protein sequence expressed by modified MSCs comprises SEQ ID NO: 1 as seen in Table 1. In some instances, the IL-12 polypeptide comprises at least a portion having at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 amino acid residues of SEQ ID NO: 1. In some cases, the IL-12 polypeptide comprises 10-90%, 20-80%, 30-70%, and 40-60% of SEQ ID NO: 1. In some instances, the IL-12 polypeptide comprises at least 10%, at least 20%, at least 30%, at least 40%, at least 50%, at least 60%, at least 70%, at least 80%, at least 90%, or at least 95% of SEQ ID NO: 1. The IL-12 polypeptide, in some cases, comprises about 10%, about 20%, about 30%, about 40%, about 50%, about 60%, about 70%, about 80%, about 90%, or about 95% of SEQ ID NO: 1. In some instances, the IL-12 polypeptide comprises at least 10%, at least 20%, at least 30%, at least 40%, at least 50%, at least 60%, at least 70%, at least 80%, at least 90%, or at least 95% sequence identity of a sequence comprising SEQ ID NO: 1. In some instances, the IL-12 polypeptide comprises at least or about 95% homology to SEQ ID NO: 1. In some instances, the IL-12 polypeptide comprises at least or about 97% homology to SEQ ID NO: 1. In some embodiments, the IL-12 polypeptide comprises at least or about 99% homology to SEQ ID NO: 1. In some instances, the IL-12 polypeptide comprises at least or about 100% homology to SEQ ID NO: 1.

Provided herein are stem cells genetically modified to express an apoptotic agent. In some instances, the apoptotic agent is an inducible caspase. In some instances, the caspase is caspase 9. An exemplary caspase 9 protein sequence expressed by modified MSCs comprises SEQ ID NO: 2 or 3. In some instances, the caspase 9 polypeptide comprises at least a portion having at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 amino acid residues of SEQ ID NO: 2 or 3. In some cases, the caspase 9 polypeptide comprises 10-90%, 20-80%, 30-70%, and 40-60% of SEQ ID NO: 2 or 3. In some instances, the caspase 9 polypeptide comprises at least 10%, at least 20%, at least 30%, at least 40%, 50%, at least 60%, at least 70%, at least 80%, at least 90%, or at least 95% of SEQ ID NO: 2 or 3. The caspase 9 polypeptide, in some cases, comprises about 10%, about 20%, about 30%, about 40%, about 50%, about 60%, about 70%, about 80%, about 90%, or about 95% of SEQ ID NO: 2 or 3. In some instances, the caspase 9 polypeptide comprises at least 10%, at least 20%, at least 30%, at least 40%, at least 50%, at least 60%, at least 70%, at least 80%, at least 90%, or at least 95% sequence identity of a sequence comprising SEQ ID NO: 2 or 3. In some instances, the caspase 9 polypeptide comprises at least or about 95% homology to SEQ ID NO: 2 or 3. In some instances, the caspase 9 polypeptide comprises at least or about 9'7% homology to SEQ ID NO: 2 or 3. In some embodiments, the caspase 9 polypeptide comprises at least or about 99% homology to SEQ ID NO: 2 or 3. In some instances, the caspase 9 polypeptide comprises at least or about 100% homology to SEQ ID NO: 2 or 3.

In some instances, a human IL-12 protein sequence expressed by modified MSCs comprises SEQ ID NO: 4 as seen in Table 2. In some instances, the IL-12 polypeptide comprises at least a portion having at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, or 320 amino acid residues of SEQ ID NO: 4. In some cases, the IL-12 polypeptide comprises 10-90%, 20-80%, 30-70%, or 40-60% of SEQ ID NO: 4. In some instances, the IL-12 polypeptide comprises at least 10%, at least 20%, at least 30%, at least 40%, 50%, at least 60%, at least 70%, at least 80%, at least 90%, or at least 95% of SEQ ID NO: 4. The IL-12 polypeptide, in some cases, comprises about 10%, about 20%, about 30%, about 40%, about 50%, about 60%, about 70%, about 80%, about 90%, or about 95% of SEQ ID NO: 4. In some instances, the IL-12 polypeptide comprises at least 10%, at least 20%, at least 30%, at least 40%, at least 50%, at least 60%, at least 70%, at least 80%, at least 90%, or at least 95% sequence identity of a sequence comprising SEQ ID NO: 4. In some instances, the IL-12 polypeptide comprises at least or about 95% homology to SEQ ID NO: 4. In some instances, the IL-12 polypeptide comprises at least or about 97% homology to SEQ ID NO: 4. In some embodiments, the IL-12 polypeptide comprises at least or about 99% homology to SEQ ID NO: 4. In some instances, the IL-12 polypeptide comprises at least or about 100% homology to SEQ ID NO: 4.

In some instances, a human IL-12 protein sequence expressed by modified MSCs comprises SEQ ID NO: 5 as seen in Table 2. In some instances, the IL-12 polypeptide comprises at least a portion having at least 10, 20, 30, 40, 50, 60, 70, 80, 90, 100, 110, 120, 130, 140, 150, 160, 170, 180, 190, 200, 210, 220, 230, 240, or 250 amino acid residues of SEQ ID NO: 5. In some cases, the IL-12 polypeptide comprises 10-90%, 20-80%, 30-70%, or 40-60% of SEQ ID NO: 5. In some instances, the IL-12 polypeptide comprises at least 10%, at least 20%, at least 30%, at least 40%, at least 50%, at least 60%, at least 70%, at least 80%, at least 90%, or at least 95% of SEQ ID NO: 5. The IL-12 polypeptide, in some cases, comprises about 10%, about 20%, about 30%, about 40%, about 50%, about 60%, about 70%, about 80%, about 90%, or about 95% of SEQ ID NO: 5. In some instances, the IL-12 polypeptide comprises at least 10%, at least 20%, at least 30%, at least 40%, at least 50%, at least 60%, at least 70%, at least 80%, at least 90%, or at least 95% sequence identity of a sequence comprising SEQ ID NO: 5. In some instances, the IL-12 polypeptide comprises at least or about 95% homology to SEQ ID NO: 5. In some instances, the IL-12 polypeptide comprises at least or about 97% homology to SEQ ID NO: 5. In some embodiments, the IL-12 polypeptide comprises at least or about 99% homology to SEQ ID NO: 5. In some instances, the IL-12 polypeptide comprises at least or about 100% homology to SEQ ID NO: 5.

In some instances, a human caspase 9 protein sequence expressed by modified MSCs comprises SEQ ID NO: 6 as seen in Table 2. In some instances, the caspase 9 polypeptide comprises at least a portion having at least 10, 20, 30, 40, 50, 60, 70, 80, 90, 100, 110, 120, 130, 140, 150, 160, 170, 180, 190, 200, 210, 220, 230, 240, 250, 260, 270, or 280 amino acid residues of SEQ ID NO: 6. In some cases, the caspase 9 polypeptide comprises 10-90%, 20-80%, 30-70%, or 40-60% of SEQ ID NO: 6. In some instances, the caspase 9 polypeptide comprises at least 10%, at least 20%, at least 30%, at least 40%, at least 50%, at least 60%, at least 70%, at least 80%, at least 90%, or at least 95% of SEQ ID NO: 6. The caspase 9 polypeptide, in some cases, comprises about 10%, about 20%, about 30%, about 40%, about 50%, about 60%, about 70%, about 80%, about 90%, or about 95% of SEQ ID NO: 6. In some instances, the caspase 9 polypeptide comprises at least 10%, at least 20%, at least 30%, at least 40%, at least 50%, at least 60%, at least 70%, at least 80%, at least 90%, or at least 95% sequence identity of a sequence comprising SEQ ID NO: 6. In some instances, the caspase 9 polypeptide comprises at least or about 95% homology to SEQ ID NO: 6. In some instances, the caspase 9 polypeptide comprises at least or about 97% homology to SEQ ID NO: 6. In some embodiments, the caspase 9 polypeptide comprises at least or about 99% homology to SEQ ID NO: 6. In some instances, the caspase 9 polypeptide comprises at least or about 100% homology to SEQ ID NO: 6.

TABLE 1

Amino Acid Sequences

| Protein | SEQ ID NO. | Amino Acid Sequence |
|---|---|---|
| hIL-12p70 fusion protein | 1 | MCHQQLVISWFSLVFLASPLVAIWELKKDVYVVELDWYPDAPGE MVVLTCDTPEEDGITWTLDQSSEVLGSGKTLTIQVKEFGDAGQYTC HKGGEVLSHSLLLLHKKEDGIWSTDILKDQKEPKNKTFLRCEAKN YSGRFTCWWLTTISTDLTFSVKSSRGSSDPQGVTCGAATLSAERVR GDNKEYEYSVECQEDSACPAAEESLPIEVMVDAVHKLKYENYTSS FFIRDIIKPDPPKNLQLKPLKNSRQVEVSWEYPDTWSTPHSYFSLTF CVQVQGKSKREKKDRVFTDKTSATVICRKNASISVRAQDRYYSSS WSEWASVPCSVPGVGVPGVGARNLPVATPDPGMFPCLHHSQNLL RAVSNMLQKARQTLEFYPCTSEEIDHEDITKDKTSTVEACLPLELTK NESCLNSRETSFITNGSCLASRKTSFMMALCLSSIYEDLKMYQVEF KTMNAKLLMDPKRQIFLDQNMLAVIDELMQALNFNSETVPQKSSL EEPDFYKTKIKLCILLHAFRIRAVTIDRVMSYLNAS |
| iCaspase9 | 2, 7, and 8, respectively, in order of appearance | TFPKRGQTCVVHYTGMLEDGKKVDSSRDRNKPFKFMLGKQEVIR GWEEGVAQMSVGQRAKLTISPDYAYGATGHPGIIPPHATLVFDVEL LKLESGGGSGVDGFGDVGALESLRGNADLAYILSMEPCGHCLIINN VNFCRESGLRTRTGSNIDCEKLRRRFSSLHFMVEVKGDLTAKKMV LALLELAQQDHGALDCCVVVILSHGCQASHLQFPGAVYGTDGCPV SVEKIVNIFNGTSCPSLGGKPKLFFIQACGGEQKDHGFEVASTSPED ESPGSNPEPDATPFQEGLRTFDQLDAISSLPTPSDIFVSYSTFPGFVS WRDPKSGSWYVETLDDIFEQWAHSEDLQSLLLRVANAVSVKGIYK QMPGCFNFLRKKLFFKTSVDYPYDVPDYALD*EFLID*PDPDMIRYI DEFGQT<br>*Potential Stop Sites |
| iCaspase9 | 3 | MLEGVQVETISPGDGRTFPKRGQTCVVHYTGMLEDGKKVDSSRDR NKPFKFMLGKQEVIRGWEEGVAQMSVGQRAKLTISPDYAYGATG HPGIIPPHATLVFDVELLKLESGGGSGVDGFGDVGALESLRGNADL AYILSMEPCGHCLIINNVNFCRESGLRTRTGSNIDCEKLRRRFSSLHF MVEVKGDLTAKKMVLALLELAQQDHGALDCCVVVILSHGCQASH LQFPGAVYGTDGCPVSVEKIVNIFNGTSCPSLGGKPKLFFIQACGGE QKDHGFEVASTSPEDESPGSNPEPDATPFQEGLRTFDQLDAISSLPT PSDIFVSYSTFPGFVSWRDPKSGSWYVETLDDIFEQWAHSEDLQSL LLRVANAVSVKGIYKQMPGCFNFLRKKLFFKTSVD<u>YPYDVPDYAL</u> <u>D</u>*<br>*Potential Stop Sites |

Bold indicates elastin linker
Underline indicates HA tag

TABLE 2

Amino Acid Sequences

| Protein | SEQ ID NO. | Gene Accession Number | Amino Acid Sequence |
|---|---|---|---|
| IL-12 subunit beta precursor | 4 | NP_002178.2 | MCHQQLVISWFSLVFLASPLVAIWELKKDVYVV ELDWYPDAPGEMVVLTCDTPEEDGITWTLDQSS EVLGSGKTLTIQVKEFGDAGQYTCHKGGEVLSH SLLLLHKKEDGIWSTDILKDQKEPKNKTFLRCEA KNYSGRFTCWWLTTISTDLTFSVKSSRGSSDPQG VTCGAATLSAERVRGDNKEYEYSVECQEDSACP AAEESLPIEVMVDAVHKLKYENYTSSFFIRDIIKP DPPKNLQLKPLKNSRQVEVSWEYPDTWSTPHSY FSLTFCVQVQGKSKREKKDRVFTDKTSATVICRK NASISVRAQDRYYSSSWSEWASVPCS |
| IL-12 subunit alpha precursor | 5 | NP_000873.2 | MWPPGSASQPPPSPAAATGLHPAARPVSLQCRLS MCPARSLLLVATLVLLDHLSLARNLPVATPDPG MFPCLHHSQNLLRAVSNMLQKARQTLEFYPCTS EEIDHEDITKDKTSTVEACLPLELTKNESCLNSRE TSFITNGSCLASRKTSFMMALCLSSIYEDLKMYQ VEEKTMNAKLLMDPKRQIELDQNMLAVIDELMQ ALNFNSETVPQKSSLEEPDFYKTKIKLCILLHAFRI RAVTIDRVMSYLNAS |
| Caspase 9 | 6 | NP_001220.2 | GSGGFGDVGALESLRGNADLAYILSMEPCGHCLI INNVNFCRESGLRTRTGSNIDCEKLRRRFSSLHFM VEVKGDLTAKKMVLALLELAQQDHGALDCCVV VILSHGCQASHLQFPGAVYGTDGCPVSVEKIVNI FNGTSCPSLGGKPKLFFIQACGGEQKDHGFEVAS TSPEDESPGSNPEPDATPFQEGLRTFDQLDAISSLP TPSDIFVSYSTFPGFVSWRDPKSGSWYVETLDDIF EQWAHSEDLQSLLLRVANAVSVKGIYKQMPGCF NFLRKKLFFKTS |

Provided herein are methods and compositions comprising genetically modified stem cells for therapeutic use. In some instances, prior to therapeutic use, genetically modified stem cells are tested for sterility, specificity, and viability. The testing may occur before shipping or storing the genetically modified stem cells. The testing may occur after shipping or storing the genetically modified stem cells. In some instances, the methods comprise measuring expression level of IL-12p70 in MSCs, either at the RNA or protein level. The expression level of IL-12p70 in MSCs produced by the methods disclosed herein may be at least about two times greater than MSCs produced/stored/shipped by traditional methods. The expression level of IL-12p70 in MSCs produced by the methods disclosed herein may be at least about two times greater than MSCs produced/stored/shipped by traditional methods. The expression level of IL-12p70 in MSCs may be at least 10%, at least 20%, at least 30%, at least 40%, at least 50%, at least 60%, at least 70%, at least 80%, at least 90%, at least 95%, or greater than 95% compared to MSCs produced/stored/shipped by traditional methods.

Provided herein are compositions of genetically modified stem cells transformed to express at least one anti-tumor agent and at least one regulatory agent to treat cancer. In some instances, the genetically modified stem cells are transformed using viral vector delivery systems. For example, the genetically modified stem cells are transformed using at least one of an adenovirus, an adeno-associated virus, and a lentivirus. Adenoviral vectors or other viral based vectors are convenient methods of gene delivery and are suitable tools to achieve long-term gene transfer. Viral vectors are advantageous in that they can transduce non-proliferating cells and they have low immunogenicity. Adenoviral vectors also do not integrate into the genome of the target cell thereby bypassing negative integration-related events. In some instances, the genetically modified stem cells are transformed using non-viral vector delivery systems. Non-viral vector delivery systems include, but are not limited to, DNA plasmids, RNA, naked nucleic acid, and nucleic acid complexed with a delivery vehicle, such as a liposome.

Provided herein, in certain embodiments, are compositions comprising genetically modified stem cells that are packaged in a kit. In some cases, the kit contains genetically modified stem cells transformed with human IL-12 and iCasp9. The kit may be single-use or reusable. In some instances, kits are provided for administration to a subject in need thereof.

In some instances, kits comprise a population of genetically modified stem cells. In some instances, the population of genetically modified stem cells is aliquoted in a suitable amount for administration to a subject in need thereof. In some instances, the amount of genetically modified stem cells is at least or about 100 cells, 1,000 cells, 10,000 cells, 100,000 cells, 1,000,000 cells, 10,000,000 cells, 100,000,000 cells, 1,000,000,000 cells, or more than 1 billion cells. In some instances, the amount of genetically modified stem cells is in a range of at least a minimum of about 10,000 to 100,000, 10,000 to 200,000, 10,000 to 400,000, 10,000 to 600,000, 10,000 to 800,000, 10,000 to 1,000,000, 10,000 to 1,500,000, 10,000 to 2,000,000, 100,000 to 200,000, 100,000 to 400,000, 100,000 to 600,000, 100,000 to 800,000, 100,000 to 1,000,000, 100,000 to 1,500,000, 100,000 to 2,000,000, 200,000 to 400,000, 200,000 to 600,000, 200,000 to 800,000, 200,000 to 1,000,000, 200,000 to 1,500,000, 200,000 to 2,000,000, 400,000 to 600,000, 400,000 to 800,000, 400,000 to 1,000,000, 400,000 to 1,500,000, 400,000 to 2,000,000, 600,000 to 800,000, 600,000 to 1,000,000, 600,000 to 1,500,000, 600,000 to 2,000,000, 800,000 to 1,000,000, 800,000 to 1,500,000, 800,000 to 2,000,000, 1,000,000 to 1,500,000, 1,000,000 to 2,000,000, or 1,500,000 to 2,000,000 stem cells.

Kits described herein comprising a population of genetically modified stem cells are administered to a subject in need thereof in a suitable dose. In some instances, a dose of genetically modified stem cells for administration is in a range of about 500,000 cells/kg to about 1,000,000 cells/kg. In some instances, the dose of genetically modified stem cells is in a range of at least a minimum of about 10,000 to 100,000, 10,000 to 200,000, 10,000 to 400,000, 10,000 to 600,000, 10,000 to 800,000, 10,000 to 1,000,000, 10,000 to 1,500,000, 10,000 to 2,000,000, 100,000 to 200,000, 100,000 to 400,000, 100,000 to 600,000, 100,000 to 800,000, 100,000 to 1,000,000, 100,000 to 1,500,000, 100,000 to 2,000,000, 200,000 to 400,000, 200,000 to 600,000, 200,000 to 800,000, 200,000 to 1,000,000, 200,000 to 1,500,000, 200,000 to 2,000,000, 400,000 to 600,000, 400,000 to 800,000, 400,000 to 1,000,000, 400,000 to 1,500,000, 400,000 to 2,000,000, 600,000 to 800,000, 600,000 to 1,000,000, 600,000 to 1,500,000, 600,000 to 2,000,000, 800,000 to 1,000,000, 800,000 to 1,500,000, 800,000 to 2,000,000, 1,000,000 to 1,500,000, 1,000,000 to 2,000,000, or 1,500,000 to 2,000,000 cells/kg.

In some instances, kits comprise a population of genetically modified stem cells, wherein the genetically modified stem cells are aliquoted in a relevant pharmaceutical composition for administration. For example, the genetically modified cells are provided as a pharmaceutically acceptable formulation, gaseous, liquid, solid, or mixture thereof that are suitable for one or more routes of administration. In some instances, the genetically modified stem cells are provided in a solution. In some instances, the pharmaceutically acceptable composition includes, but not limited to, (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

In some instances, kits comprise a population of genetically modified stem cells, wherein the genetically modified stem cells are aliquoted in a suitable container for administration. For example, stem cells are aliquoted in storage units or containers for storing genetically modified stem cells produced by methods described herein, wherein the storage units comprises an inner surface, wherein the inner surface is a surface of the storage units that is in contact with cells stored therein. Exemplary inner surface material is hard plastic or glass. The inner surface may be absent of any polymers that would be taken up by, and/or induce a response in, cells stored within the storage unit. The inner surface may be constructed of polymers that are not taken up by genetically modified stem cells or any cells stored within the storage unit. The inner surface may be free or essentially free of any polymers that would be taken up by, and/or induce a response in, cells stored within the storage unit. The inner surface may be essentially free of any polymers that would be taken up by, and/or induce a response in, cells stored within the storage unit. The inner surface may be at least 90%, at least 95%, at least 98%, or at least 99% free of any polymers that would be taken up by, and/or induce a response in, cells stored within the storage unit following addition of cells and storage media. The inner surface may be at least 99.5%, at least 99.6%, at least 99.7%, at least 99.8%, or at least 99.9% free of any polymers that would be taken up by, and/or induce a response in, cells stored within the storage unit following addition of cells and storage media.

In some instances, the storage units are suitable for freezing at a temperature as low as −70° C. In some instances, the storage units are suitable for freezing at a temperature lower than −70° C. In some instances, the storage units are suitable for freezing in liquid $N_2$. In some instances, the storage units are suitable for freezing at −20° C. In some instances, the storage units are suitable for a temperature of 4° C. In some instances, the storage units are suitable for storage for a certain time, for example, for storage up to 1 year. In some instances, the storage units are suitable for shipping to the clinic for use. In some instances, genetically modified stem cells are stored using cryoprotectants such as DMSO, glycerol, polyethylene glycol, propylene glycol, glycerine, polyvinylpyrolidone, sorbitol, dextran, and trehalose. Genetically modified stem cells in some cases are stored for at least 1 day, at least 1 week, at least 1 month, at least 2 months, at least 3 months, at least 4 months, at least 5 months, at least 6 months, at least 7 months, at least 8 months, at least 9 months, at least 10 months, at least 11 months, at least 1 year, or more than 1 year. In some instances, genetically modified stem cells are stored for up to 1 day, up to 1 week, up to 1 month, up to 2 months, up to 3 months, up to 4 months, up to 5 months, up to 6 months, up to 7 months, up to 8 months, up to 9 months, up to 10 months, up to 11 months, up to 1 year, or more than 1 year. Methods described herein, in some cases, comprise storing and/or shipping genetically modified stem cells in a storage unit. In some instances, methods comprise shipping cells cool overnight. In some cases, methods comprise thawing or warming cells to 37° C. (e.g., in a warm-water bath).

Provided herein are delivery units for genetically modified stem cells produced by methods described herein. Exemplary delivery units for genetically modified stem cells include tubes, syringes, vials, bags, cell culture plates, porous dissolvable packets, and other devices that can receive cells. In some instances, genetically modified stem cells are packaged in a delivery unit suitable for administration to a subject. For example, genetically modified stem cells are packaged into a syringe for administration to a subject either, subcutaneously, intravenously, intramuscularly, or intraperitoneally. In some instances, genetically modified stem cells are used to form pharmaceutical compositions having a pharmaceutically acceptable carrier such as buffered saline solution.

In some instances, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

In some instances, kits comprise one or more additional containers, each with one or more of various materials (such as reagents, optionally in concentrated form, and/or devices) desirable from a commercial and user standpoint for use of described herein. Non-limiting examples of such materials include, but not limited to, buffers, primers, enzymes, diluents, filters, carrier, package, container, vial and/or tube labels listing contents and/or instructions for use and package inserts with instructions for use. A set of instructions is optionally included. In some instances, a label is on or associated with the container. In some instances, a label is on a container when letters, numbers or other characters forming the label are attached, molded or etched into the container itself; a label is associated with a container when it is present within a receptacle or carrier that also holds the container, e.g., as a package insert. In other cases, a label is used to indicate that the contents are to be used for a specific therapeutic application. In some instances, a label also indicates directions for use of the contents, such as in the methods described herein.

Methods of Treatment

Described herein are methods and compositions relating to cancer therapies. Some methods comprise genetically modified stem cells that express at least one anti-tumor agent and at least one regulatory agent. The anti-tumor agent is often involved in modulating an immune response of an individual in which it is expressed so as to increase T cell activity, decrease wound healing, or both. A regulatory agent is an agent that induces apoptosis or otherwise induces cell death in response to a signal such as a small molecule. Described herein are methods and compositions relating to modified human MSC-based cancer immunotherapies. Exemplary sources of MSCs are human term placentas or adult bone marrow. In some instances, the human IL-12 gene is transformed into MSCs and promotes T cell activation. The methods and compositions as described herein promote wound clearance and modify the wound site as to create an environment amenable to an immune response rather than a wound healing response. To mitigate potential clinical adverse effects, genetically modified stem cells can contain a regulatory agent comprising an apoptotic protein or other protein whose expression or activation results in cell death. Examples of such proteins include any protein which, by its expression or activation, induces cell death, such as a DNase, RNase, protease, ATPase, transcription inhibitor, translation inhibitor, cell cycle inhibitor, cell checkpoint progression inhibitor, kinase or kinase inhibitor, protease inhibitor, a cell or organellar membrane integrity-modifying enzyme, a respiratory chain regulator, a modulator of protein folding, assembly, localization or processing, or other enzyme that triggers cell death directly or through eliciting a cell's own cell death pathway.

Some suicide proteins are regulated transcriptionally, so that they are only transcribed upon receipt of a signal, such as a stress, a small molecule, or a positional signal such as presence in a healed wound site.

Alternately or in combination, some suicide proteins are regulated post-transcriptionally. Examples of post-transcriptional regulation include regulation at the level of translation, localization, or activity. For example, some suicide proteins are regulated at the level of multimer formation such as homodimer or heterodimer formation. This regulation is native or, alternately, is effected through the addition of a regulatable dimerization domain. The dimerization domain is regulated by, for example heat shock, cold, phosphorylation, transcription of a positional regulator, or preferably in some cases, administration of a small molecule that triggers dimerization.

Exemplary suicide proteins that can be regulated by multimer formation include, but are not limited to, caspase 1, caspase 3, caspase 6, caspase 7, caspase 8, caspase 9, and Fas. In some instances, the suicide protein is regulated by dimerization or multimerization of protein domains, such as domains added to the cell-death inducing moiety, protein or protein fragment. Exemplary proteins or domains thereof that can multimerize or dimerize include, but are not limited to, FK506-binding protein (FKBP), calcineurin A, cyclophilin, FKBP-rapamycin binding domain of FKPB, B subunit of bacterial DNA gyrase, dihydrofolate reductase, and Fas domains. In some instances, the protein or domains thereof is modified so as to be receptive to binding of small molecules that cause multimerization or dimerization and subsequent cell death. For example, FKBP12-F36V comprises a FKBP domain with an amino acid substitution at residue 36 of phenylalanine for valine, which allows for small-molecule induced dimerization. Exemplary dimerization protein domains are seen in Table 3.

TABLE 3

| Dimerizing Proteins | Dimerizing agent |
| --- | --- |
| FKBP: FKBP | FK1012 |
| FKBP: CalcineurinA (CNA) | FK506 |
| FKBP: CyP-Fas | FKCsA |
| FKBP: FRB domain of mTOR | Rapamycin |
| GyrB: GyrB | Coumermycin |
| GAI: GID1 | Gibberellin |

In some instances, suicide proteins induce cell death by converting a nontoxic compound to a toxic compound. In some instances, the suicide protein phosphorylates nucleosides that then incorporate into DNA and lead to chain termination and cell death. In some instances, suicide proteins include, but are not limited to, herpes simplex virus thymidine kinase (HSV-TK) and cytosine deaminse (CD).

In some instances, suicide proteins induce cell death via an antibody mediated mechanism. In some cases, an exogenous signal causes complement/antibody dependent cell death. Exemplary complement/antibody dependent cell death targets are CD20, RQR8, c-myc, and EGFR. In some instances, cell death is induced using an antibody directed to a surface marker unique to stem cells such as MSCs.

In some preferred embodiments, the suicide protein is encoded by an inducible apoptotic signaling protein, such as a caspase-9 suicide gene. In some instances, the expression of the caspase-9 suicide gene is inducible. In some instances, the activity of the caspase-9 suicide protein is inducible, such as by small-molecule induced dimerization.

The compositions and methods described herein are used in the treatment of cancer. The term "cancer" as used herein is defined as a hyperproliferation of cells that exhibit one or more of unregulated growth, lack of differentiation, local tissue invasion, and metastasis, or are otherwise understood as cancer.

In some instances, cancer targeted herein is a palpable tumor excisable by surgery. Consistent with the application, cancer treatments as described herein target cancer cells that remain following surgery, chemotherapy, or radiation. Cancer therapies using methods and compositions as described herein promote wound clearance and modify the wound site as to promote an immune response rather than a wound healing response. Mechanisms that promote wound healing have been shown to promote growth and proliferation of malignant cells. By promoting an immune response rather than a wound healing response, a subject's immune system is stimulated to target and kill cancer cells. Exemplary cancers treated using methods and compositions as described herein are breast cancer, colon cancer, rectal cancer, lung cancer, ovarian cancer, prostate cancer, skin cancer, brain cancer, bladder cancer, endometrial cancer, kidney cancer, pancreatic cancer, thyroid cancer, and melanoma. Exemplary cancer cells include, but are not limited to, carcinoma, melanoma, leukemia, fibrosarcoma, sarcoma, adenocarcinoma, and glioma.

Provided herein are methods for treatment of a condition in a subject comprising administering genetically modified stem cells to a subject in need thereof, wherein the genetically modified stem cells are provided as a pharmaceutical acceptable composition. In some instances, the genetically modified cells are provided as a pharmaceutically acceptable formulation, gaseous, liquid, solid, or mixture thereof that are suitable for one or more routes of administration. In some instances, the genetically modified stem cells are provided in a solution. In some instances, the pharmaceutically acceptable composition includes, but not limited to, solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

In some instances, genetically modified stem cells are provided as a composition or formulation comprising a biopolymer. In some instances, the biopolymer is a polymerizable or crosslinkable material. Exemplary polymerizable or crosslinkable material include, but are not limited to, polyanionic polysaccharides (e.g., hyaluronic acid (HA)), carboxymethylcellulose (CMC), carboxymethylamylose (CMA), chondroitin-6-sulfate, dermatin sulfate, dermatin-6-sulfate, alginic acid, chitin, chitosan, fibrin, dextran, polylactic acid, polyglycolic acid, poly(D-)lactic acid, polyglycoliclactic acid, keratin, laminin, elastin, collagen and other naturally-occurring extracellular matrix proteins, gelatin, polydioxanones, polycaprolactone, and blends and co-polymers thereof. In some instances, the biopolymer improves MSC's ability to engraft at a target site. In some instances, the biopolymer forms a scaffold, wherein genetically modified stem cells are loaded. In some embodiments, the scaffold is biocompatible and allows the genetically modified stem cells to migrate to the target site. In some instances, the target site is a tumor site or a site of damaged tissue. In some instances, genetically modified stem cells comprising the biopolymer are administered intracavity after surgical removal of a tumor. In some instances, genetically modified stem cells comprising the biopolymer are administered after treatment by chemotherapy or radiation.

Provided herein are methods for treatment of a condition in a subject comprising administering genetically modified stem cells to a subject in need thereof, wherein the stem cells are autologous. In some instances, the stem cells are autologous since the stem cells are obtained from the same individual. In some instances, autologous mesenchymal stem cells are isolated from a subject and genetically modified prior to administration to the subject. In some instances, the autologous mesenchymal stem cells are isolated from a subject and genetically modified prior to at least one of surgery, chemotherapy, or radiation.

Provided herein are methods for treatment of a condition in a subject comprising administering genetically modified stem cells to a subject in need thereof, wherein the stem cells are allogeneic. In some cases, the genetically modified stem cells are allogeneic since the stem cells are obtained from another individual. In some instances, allogeneic stem cells are administered to a subject in need thereof. In some instances, the allogeneic stem cells are derived from a third party donor. In some instances, the allogeneic stem cells of the third party donor are isolated from a subject prior to treatment, during treatment, or after treatment. In some instances, allogeneic mesenchymal stem cells of the third party donor are isolated and genetically modified prior to administration to the subject. In some instances, the allogeneic mesenchymal stem cells are isolated from a subject and genetically modified prior to at least one of surgery, chemotherapy, or radiation.

In some instances, the allogeneic or autologous stem cells are isolated, genetically modified, and administered directly to a subject in need thereof. In some instances, the allogeneic or autologous stem cells are isolated, genetically modified, and frozen until treatment to a subject in need thereof. In some instances, compositions of genetically modified stem cells are frozen prior to administration to the subject. The term "frozen" includes compositions at temperatures at which the composition is in a solid form or semi-solid form. Frozen may include compositions at temperatures of less than 0° C., and less than −15° C. In some instances, stocks of compositions of genetically modified stem cells are frozen prior to administration to the subject. In some instances, when the subject requires treatment, the compositions of genetically modified stem cells are thawed. For example, the compositions of genetically modified stem cells are administered to the subject within at least or about 5 minutes, 10 minutes, 20 minutes, 30 minutes, 1 hour, 2 hours, 3 hours, 4 hours, 5 hours, 6 hours, 7 hours, 8 hours, 9 hours, 10 hours, or more than 10 hours of being thawed. In some instances, the compositions of genetically modified stem cells are administered to the subject within at most 5 minutes, 10 minutes, 20 minutes, 30 minutes, 1 hour, 2 hours, 3 hours, 4 hours, 5 hours, 6 hours, 7 hours, 8 hours, 9 hours, or 10 hours of being thawed.

Sometimes methods comprise administering the genetically modified stem cells such as MSCs after they have been isolated and modified, without storing or shipping. In some cases, the methods comprise administering the genetically modified stem cells after storing or shipping them. In some instances, the methods comprise administering genetically modified stem cells at least 1 hour, at least 2 hours, at least 6 hours, at least 12 hours, at least 24 hours, at least 1 day, at least 2 days, at least 3 days, at least 5 days, at least 1 week, at least 2 weeks, at least 1 month, at least 2 months, at least 3 months, at least 4 months, at least 6 months, at least 8 months, at least 12 months, or more after isolation and modification. Sometimes methods comprise administering genetically modified stem cells up to 1 hour, up to 2 hours, up to 6 hours, up to 12 hours, up to 24 hours, up to 1 day, up to 2 days, up to 3 days, up to 5 days, up to 1 week, up to 2 weeks, up to 1 month, up to 2 months, up to 3 months, up to 4 months, up to 6 months, up to 8 months, up to 12 months, or up to 24 months after isolation and modification.

Compositions of genetically modified stem cells variously comprise at least 100 cells, 1,000 cells, 10,000 cells, 100,000 cells, 1,000,000 cells, 10,000,000 cells, 100,000,000 cells, 1,000,000,000 cells, or more than 1 billion cells. Compositions of genetically modified stem cells variously comprises administration of up to about 100 cells, up to about 1,000 cells, up to about 10,000 cells, up to about 100,000 cells, up to about 1,000,000 cells, up to about 10,000,000 cells, up to about 100,000,000 cells, up to about 1,000,000,000 cells, or up to about 1 billion cells. In some instances, compositions of genetically modified stem cells comprises administration of a range of at least a minimum of about 10,000 to 100,000, 10,000 to 200,000, 10,000 to 400,000, 10,000 to 600,000, 10,000 to 800,000, 10,000 to 1,000,000, 10,000 to 1,500,000, 10,000 to 2,000,000, 100,000 to 200,000, 100,000 to 400,000, 100,000 to 600,000, 100,000 to 800,000, 100,000 to 1,000,000, 100,000 to 1,500,000, 100,000 to 2,000,000, 200,000 to 400,000, 200,000 to 600,000, 200,000 to 800,000, 200,000 to 1,000,000, 200,000 to 1,500,000, 200,000 to 2,000,000, 400,000 to 600,000, 400,000 to 800,000, 400,000 to 1,000,000, 400,000 to 1,500,000, 400,000 to 2,000,000, 600,000 to 800,000, 600,000 to 1,000,000, 600,000 to 1,500,000, 600,000 to 2,000,000, 800,000 to 1,000,000, 800,000 to 1,500,000, 800,000 to 2,000,000, 1,000,000 to 1,500,000, 1,000,000 to 2,000,000, or 1,500,000 to 2,000,000 stem cells.

Compositions described herein comprise a suitable dose of genetically modified stem cells for administration to a subject in need thereof. In some instances, a dose of genetically modified stem cells for administration is in a range of about 500,000 cells/kg to about 1,000,000 cells/kg. In some instances, the dose of genetically modified stem cells is in a range of at least a minimum of about 10,000 to 100,000, 10,000 to 200,000, 10,000 to 400,000, 10,000 to 600,000, 10,000 to 800,000, 10,000 to 1,000,000, 10,000 to 1,500,000, 10,000 to 2,000,000, 100,000 to 200,000, 100,000 to 400,000, 100,000 to 600,000, 100,000 to 800,000, 100,000 to 1,000,000, 100,000 to 1,500,000, 100,000 to 2,000,000, 200,000 to 400,000, 200,000 to 600,000, 200,000 to 800,000, 200,000 to 1,000,000, 200,000 to 1,500,000, 200,000 to 2,000,000, 400,000 to 600,000, 400,000 to 800,000, 400,000 to 1,000,000, 400,000 to 1,500,000, 400,000 to 2,000,000, 600,000 to 800,000, 600,000 to 1,000,000, 600,000 to 1,500,000, 600,000 to 2,000,000, 800,000 to 1,000,000, 800,000 to 1,500,000, 800,000 to 2,000,000, 1,000,000 to 1,500,000, 1,000,000 to 2,000,000, or 1,500,000 to 2,000,000 cells/kg.

Provided herein are methods for treatment of a condition in a subject comprising administering genetically modified stem cells to a subject in need thereof by a suitable route of administration. In some instances, genetically modified stem cells are administered systemically. In some instances, genetically modified stem cells are administered locally. In some instances, genetically modified stem cells are administered by at least one of intravenously, locally at a site of a tumor, and by infusion. In some instances, genetically modified stem cells are injected at least one of a site of tumor, a site of tumor excision, or at a site where a tumor has been removed surgically or through chemotherapy. Alternately, when a solid tumor site is not accessible by surgery or a needle, genetically modified stem cells are intravenously infused. Methods described herein may comprise suspending or mixing cells in a solution for intravenous (i.v.) administration (e.g., a 0.9% NaCl solution). In some cases, intracavitary infusion is used to administer genetically modified stem cells. In some instances, intratumor infusion is used to administer genetically modified stem cells. Infusion of genetically modified stem cells in some cases is through a catheter. In some instances, genetically modified stem cells are administered through a catheter over time. For example, genetically modified stem cells are administered through a catheter daily, multiple times weekly, weekly, biweekly, monthly, more or less frequently.

In some instances, genetically modified stem cells are administered as a vaccine. Exemplary vaccines include, but are not limited to, a DNA vaccine, a peptide vaccine, a RNA vaccine, a viral vaccine, or combinations thereof. In some instances, the vaccine comprises the genetically modified stem cells and an antigenic polypeptide relating to a cancer. In some instances, the vaccine elicits an antibody-mediated immune response in response to the antigen to target cancer. In some instances, the vaccine comprises the genetically modified stem cells only and an immune response is caused by secretion of IL-12 by the genetically modified stem cells at a cancer site. In some instances, the vaccine is formulated as a pharmaceutically acceptable formulation, gaseous, liquid or solid, or mixture thereof that are suitable for one or more routes of administration. In some instances, the vaccine is administered by a route including, but not limited to, subcutaneous, intradermal, intramuscular, intranasal, intravenous, and sublingual.

In some cases, administration of genetically modified stem cells is repeated not more than once, not more than twice, not more than three times, or not more than ten times. In some cases, administration of genetically modified stem cells is repeated more than once, more than twice, more than three times, or more than ten times. Administration of genetically modified stem cells may be repeated as often is needed.

Genetically modified stem cells in some cases are used in combination with surgery. For example, genetically modified stem cells are administered prior to tumor surgery, during tumor surgery, or following tumor surgery. In some instances, genetically modified stem cells are administered by at least one of intravenously, locally at a site of a tumor, and by infusion. In some instances, genetically modified stem cells are injected at a site of tumor excision or at a site where a tumor has been removed surgically. Administration of genetically modified stem cells in some cases prior to surgery results in a reduction in tumor load in a patient. In some cases, genetically modified stem cells are administered up to 1 day, up to 2 days, up to 3 days, up to 5 days, or more prior to surgery. Sometimes genetically modified stem cells are administered singly, or over a time course, such as daily, multiple times weekly, weekly, biweekly, monthly or less frequently prior to surgery. In some instances, genetically modified stem cells are administered singly, or over a time course, such as daily, multiple times weekly, weekly, biweekly, monthly or more frequently prior to surgery.

In some instances, administration of genetically modified stem cells is in combination with surgery or subsequently to excision of a tumor during or following surgery. Often genetically modified stem cells target remaining cancer cells around a periphery of an excised tumor. Genetically modified stem cells in some cases are administered up to 1 day, up to 2 days, up to 3 days, up to 5 days, or more than 5 days following excision of a tumor. In some cases, genetically modified stem cells are administered one week, two weeks, one month, two months, three months, four months, five months, one year, two years, three years, four years, five years, or more than five years following excision of a tumor. Sometimes genetically modified stem cells are administered singly, or over a time course, such as daily, multiple times weekly, weekly, biweekly, monthly or less frequently following excision. In some instances, genetically modified stem cells are administered singly, or over a time course, such as daily, multiple times weekly, weekly, biweekly, monthly or more frequently following excision.

Genetically modified homing cells such as modified MSCs are administered prior to chemotherapy, during chemotherapy, or following chemotherapy. Sometimes genetically modified stem cells are administered up to 1 day, up to 2 days, up to 3 days, up to 5 days, or more than 5 days prior to chemotherapy. Genetically modified stem cells in some cases are administered up to 1 day, up to 2 days, up to 3 days, up to 5 days, or more than 5 days following chemotherapy. In some instances, genetically modified stem cells are administered singly, or over a time course, such as daily, multiple times weekly, weekly, biweekly, monthly or less frequently prior to or following chemotherapy. In some instances, genetically modified stem cells are administered singly, or over a time course, such as daily, multiple times weekly, weekly, biweekly, monthly or more frequently prior to or following chemotherapy. Exemplary chemotherapy include, but are not limited to, cyclophosphamide, paclitaxel, 5-fluorouracil, 5-aza-2'-deoxycitidine, mitomycin, doxorubicin, and mitoxantrone.

In some instances, genetically modified MSCs are administered prior to radiation therapy, during radiation therapy, or following radiation therapy. In some cases, genetically modified stem cells are administered up to 1 day, up to 2 days, up to 3 days, up to 5 days, or more than 5 days prior to radiation. In some cases, genetically modified stem cells are administered up to 1 day, up to 2 days, up to 3 days, up to 5 days, or more than 5 days following radiation. Sometimes genetically modified stem cells are administered singly, or over a time course, such as daily, multiple times weekly, weekly, biweekly, monthly or less frequently prior to or following radiation. In some instances, genetically modified stem cells are administered singly, or over a time course, such as daily, multiple times weekly, weekly, biweekly, monthly or more frequently prior to or following radiation.

Alternately to surgery, chemotherapy, or radiation, genetically modified stem cells are administered in combination with a modulatory agent for an immune checkpoint. Exemplary immune checkpoint targets include, but are not limited to, 2B4 (CD244), A2aR, B7H3 (CD276), B7H4 (VTCN1), B7H6, B7RP1, BTLA (CD272), butyrophilins, CD103, CD122, CD137 (4-1BB), CD137L, CD160, CD2, CD200R, CD226, CD26, CD27, CD28, CD30, CD39, CD40, CD48, CD70, CD73, CD80 (B7.1), CD86 (B7.2), CEACAM1, CGEN-15049, CTLA-4, DR3, GALS, GITR, GITRL, HVEM, ICOS, ICOSL (B7H2), IDOL IDO2, ILT-2 (LILRB1), ILT-4 (LILRB2), KIR, KLRG1, LAG3, LAIR1 (CD305), LIGHT (TNFSF14), MARCO, NKG2A, NKG2D, OX-40, OX-40L, PD-1, PDL-1 (B7-H1, CD 274), PDL-2 (B7-DC, CD 273), PS, SIRPalpha (CD47), SLAM, TGFR, TIGIT, TIM1, TIM3 (HAVCR2), TIM4, or VISTA. An immune checkpoint modulatory agent in some cases is at least one of a small molecule, an antibody, a nucleic acid encoding an antibody, an antigen binding fragment, a RNA interfering agent, a peptide, a peptidomimetic, a synthetic ligand, and an aptamer. In some instances, an immune checkpoint inhibitor is administered. Exemplary immune checkpoint inhibitors are Enoblituzumab (e.g., MGA271), Ipilimumab (e.g., BMS-734016, MDX-010), Tremelimumab (e.g., CP-675, CP-675,206), Lirilumab (e.g., BMS-986015, IPH2102), BMS986016, Pembrolizumab (e.g., MK-3475, SCH 900475), Nivolumab (e.g., BMS-936558, MDX-1106, ONO-4538), Pidilizumab (e.g., CT-011, MDV9300), Atezolizumab (e.g., MPDL3280A, RG7446, R05541267), BMS-936559 (e.g., MDX-1105), and Bavituximab. Genetically modified stem cells in some cases are administered in combination with immunotherapy such as CAR T cell therapy.

Therapies comprising genetically modified stem cells in some instances reduce or eliminate tumor cell regrowth or proliferation at a wounding site. In some instances, a wounding site is a site where a tumor has been excised. In some cases, a wounding is a site which has been subject to chemotherapy, radiotherapy, or immunotherapy. Tumor cell regrowth or proliferation may decrease by 5-95%, 10-90%, 20-80%, 30-70%, 40-60%, 50-95%, 65-85%, or 75-95%. The decrease in tumor cell regrowth or proliferation may by at least 5%, 10%, 15%, 20%, 25%, 30%, 35%, 40%, 45%, 50%, 55%, 60%, 65%, 70%, 75%, 80%, 85%, 90%, 95%, or greater than 95%. The decrease in tumor cell regrowth or proliferation may by at least 5%. The decrease in tumor cell regrowth or proliferation may by at least 10%. The decrease in tumor cell regrowth or proliferation may by at least 30%. The decrease in tumor cell regrowth or proliferation may be by at least 50%.

In some instances, at least one of CD1, IL-2, and IL-12 is systemically downregulated prior to administration of genetically modified stem cells. In some instances, CD1, IL-2, and IL-12 are all systemically downregulated prior to administration of genetically modified stem cells. Downregulation of at least one of CD-1, IL-2, and IL-12, can enhance the efficacy of the stem cells for targeting cancer cells or a tumor.

In some instances, cancer treatment involving genetically modified MSCs comprises targeting one or more cytokine. In some instances, the cytokine is at least one of, TNF-α, IL-2, IL-15, IL-18, IFN-α, G-CSF, and GM-CSF. The cytokine Exemplary methods of targeting the cytokine include, but are not limited to, an antibody, an agonist, a nucleic acid encoding the cytokine, a small molecule, a peptide, a peptidomimetic, and a soluble version of the cytokine.

In some cases, cancer treatment involving genetically modified MSCs also includes targeting IL-2. Exemplary methods of targeting IL-2 include an IL-2 antibody, an agonist of IL-2 receptor, a nucleic acid encoding IL-2, a small molecule, a peptide, a peptidomimetic, or a soluble version of IL-2. Alternately, MSCs can be genetically modified to express at least one of IL-12 and IL-2. Targeting other cytokines can be used in combination with IL-12, in combination with IL-2, or as an alternate to IL-2 and IL-12.

In some instances, the tumor size is determined by at least one of a PET scan, a MRI, and a CT scan. Cancer is sometimes measured by blood tests to measure at least one of complete blood count, proteins in the blood, and tumor markers in the blood. In some instances, wound healing is monitored.

Often a regulatory agent such as an apoptotic agent is activated once the tumor size has decreased. In some instances, the regulatory agent is activated when the tumor size is decreased by about 5% to about 10%, about 10% to about 25%, about 25% to about 50%, about 25% to about 95%. In some instances, regulatory agent is activated when the tumor size is decreased by at least 5%, at least 10%, at least 20%, at least 30%, at least 40%, at least 50%, at least 60%, at least 70%, at least 80%, at least 90%, or at least 95%. In some cases, the regulatory agent is activated when the tumor size is decreased by about 5-95%, 10-90%, 20-80%, 30-70%, 40-60%, 50-95%, 65-85%, or 75-95%. In some cases, the regulatory agent is activated when the decrease in tumor size is by at least 5%, 10%, 15%, 20%, 25%, 30%, 35%, 40%, 45%, 50%, 55%, 60%, 65%, 70%, 75%, 80%, 85%, 90%, 95%, or more than 95%. In some instances, the regulatory agent is activated when the decrease in tumor size is at least 5%. In some cases, the regulatory agent is activated when the decrease in tumor size is at least 10%. In some instances, the regulatory agent is activated when the decrease in tumor size is at least 30%. In some instances, the regulatory agent is activated when the decrease in tumor size is at least 50%.

In some instances, a regulatory agent is activated to regulate a wounding response at a tumor site. Often use of chemotherapy or radiation mimics wounding and causes unregulated cell growth, promoting a cancer environment. In some instances, cancer cells remain in a site periphery to excision of a tumor. A regulatory agent is often activated to modulate cell death of cells at sites of chemotherapy, radiation, or surgery. In some instances, genetically modified stem cell function is modulated at a tumor site. Exemplary stem cell function that is modulated are cell death, cell growth, cell proliferation, and wounding.

Described herein are methods of modulating activity of genetically modified stem cells by administering an exogenous signal to a subject. An exemplary exogenous signal is a small molecule. In some instances, an exogenous signal is administered by at least one of intravenously, subcutaneously, and by infusion. Alternately, an exogenous signal is surgically introduced, ingested, or administered topically, orally, bucaly, or nasally. An exogenous signal in some instances is administered by infusion through a catheter. An exogenous signal can be administered singly, or over a time course, such as daily, multiple times weekly, weekly, biweekly, monthly, more or less frequently.

Provided herein are methods of modulating activity of genetically modified stem cells by administering an exogenous signal to a subject, wherein the exogenous signal is administered following introduction of the genetically modified stem cell. In some instances, the exogenous signal is administered following tumor removal. In some instances, tumor removal is by surgery. In some instances, tumor removal is by cancer treatment including, but not limited to, surgery, chemotherapy, radiation, and immunotherapy. In some instances, the exogenous signal is administered no sooner than 1 day, 2 days, 3 days, 4 days, 5 days, 6 days, 1 week, 2 weeks, 3 weeks, 4 weeks, or more than 4 weeks following tumor removal. In some instances, the exogenous signal is administered at least 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 12 months, 1 year, 2 years, 3 years, 4 years, or more than 4 years following tumor removal.

In some instances, an exogenous signal is at least one of a small molecule, an antibody, a nucleic acid encoding an antibody, an antigen binding fragment, a RNA interfering agent, a peptide, a peptidomimetic, a synthetic ligand, and an aptamer. An exogenous signal in some cases is at least one of heat shock, hypoxia, nutrient deficiency, a metal ion, and a steroid. Exemplary small molecules are FK1012, FK506, FK506-CsA, FKCsA, rapamycin, coumermycin, gibberellin, HaXS, methotrexate, AP20187, and AP1903.

In some instances, the exogenous signal is administered at a suitable dosage. In some cases, therapeutically effective amounts or dosages include dosages of about 0.01 mg/kg to 20 mg/kg, for example, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, 13 mg/kg, 13.1 mg/kg, 13.2 mg/kg, 13.3 mg/kg, 13.4 mg/kg, 13.5 mg/kg, 13.6 mg/kg, 13.7 mg/kg, 13.8 mg/kg, 13.9 mg/kg, 14 mg/kg, 14.1 mg/kg, 14.2 mg/kg, 14.3 mg/kg, 14.4 mg/kg, 14.5 mg/kg, 14.6 mg/kg, 14.7 mg/kg, 14.8 mg/kg, 14.9 mg/kg, 15 mg/kg, 15.1 mg/kg, 15.2 mg/kg, 15.3 mg/kg, 15.4 mg/kg, 15.5 mg/kg, 15.6 mg/kg, 15.7 mg/kg, 15.8 mg/kg, 15.9 mg/kg, 16 mg/kg, 16.1 mg/kg, 16.2 mg/kg, 16.3 mg/kg, 16.4 mg/kg, 16.5 mg/kg, 16.6 mg/kg, 16.7 mg/kg, 16.8 mg/kg, 16.9 mg/kg, 17 mg/kg, 17.1 mg/kg, 17.2 mg/kg, 17.3 mg/kg, 17.4 mg/kg, 17.5 mg/kg, 17.6 mg/kg, 17.7 mg/kg, 17.8 mg/kg, 17.9 mg/kg, 18 mg/kg, 18.1 mg/kg, 18.2 mg/kg, 18.3 mg/kg, 18.4 mg/kg, 18.5 mg/kg, 18.6 mg/kg, 18.7 mg/kg, 18.8 mg/kg, 18.9 mg/kg, 19 mg/kg, 19.1 mg/kg, 19.2 mg/kg, 19.3 mg/kg, 19.4 mg/kg, 19.5 mg/kg, 19.6 mg/kg, 19.7 mg/kg, 19.8 mg/kg, 19.9 mg/kg, or 20 mg/kg. Regulatorily effective amounts or dosages, in some cases, are contemplated to include dosages of about 0.1 mg/kg to about 4.0 mg/kg. In some cases, therapeutically effective amounts or dosage is more than 20 mg/kg.

In some instances, co-treatment of genetically modified stem cells with surgery decreases tumor regrowth more than surgery alone. In some cases, co-treatment of genetically modified MSCs with chemotherapy decreases the tumor regrowth more than chemotherapy treatment alone. In some instances, co-treatment of genetically modified MSCs with radiation decreases the tumor regrowth more than radiation treatment alone. Sometimes tumor regrowth decreases by about 10% to about 25%, about 10% to about 50%, about 20% to about 95%. In some instances, tumor regrowth decreases by at least 5%, at least 10%, at least 20%, at least 30%, at least 40%, at least 50%, at least 60%, at least 70%, at least 80%, at least 90%, or at least 95%. Tumor regrowth in some cases decrease by about 5-95%, 10-90%, 20-80%, 30-70%, 40-60%, 50-95%, 65-85%, or 75-95%. In some cases, the decrease in tumor regrowth is by at least 5%, 10%, 15%, 20%, 25%, 30%, 35%, 40%, 45%, 50%, 55%, 60%, 65%, 70%, 76%, 80%, 85%, 90%, 95%, or more than 95%. The decrease in tumor regrowth sometimes is at least 5%. In some cases, the decrease in tumor regrowth is by at least 10%. The decrease in tumor regrowth in some cases is at least 30%. In some instances, the decrease in tumor regrowth may be by at least 50%.

Cancers targeted herein may be a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer.

Cancer treatments as described herein can be used to treat lung cancer such as non-small cell lung carcinoma (NSCLC), small cell lung carcinoma, or mesotheliomia. Examples of NSCLC include squamous cell carcinoma, adenocarcinoma, and large cell carcinoma. In some instances, the mesothelioma is a cancerous tumor of the lining of the lung and chest cavity (pleura) or lining of the abdomen (peritoneum). In some instances, the mesothelioma is due to asbestos exposure. Mesothelioma affects the mesothelium, a protective membrane that covers internal organs of the body including the lungs, heart and abdominal organs. Mesothelioma can develop at any of these sites, but approximately 75% of the time it is the lung lining, or pleura, that is affected.

As described herein cancer therapies relating to genetically modified stem cells comprising at least one anti-tumor agent and at least one regulatory agent are often used to treat palpable tumors. Alternately, methods and compositions as described herein are used to treat a non-tumor forming cancer. An exemplary non-tumor forming cancer is blood cancer such as, by way of non-limiting example, leukemia, lymphoma, or myeloma.

Compositions and methods described herein reduce or eliminate symptoms associated with cancer. Some such symptoms are known in the art and include but are not limited to fatigue, weight loss, fever, pain, constipation, diarrhea, unusual bleeding, and other signs and symptoms of cancer, including early death. In some instances, cancer treatments described herein target mesothelioma, particularly pleural mesothelioma. Symptoms associated with pleural mesothelioma include, but are not limited to, chest wall pain, pleural effusion, shortness of breath, fatigue, anemia, wheezing, hoarseness, cough, blood in the sputum, coughing blood, or combinations thereof. In other instances, the compositions and methods described herein reduce or eliminate symptoms associated with abdominal mesothelioma. Symptoms associated with abdominal mesothelioma include, but are not limited to, abdominal pain, ascites, abdominal mass, problems with bowel function, weight loss, or combinations thereof. In further instances, the compositions and methods described herein reduce or eliminate symptoms associated with severe mesothelioma. Symptoms associated with severe mesothelioma include, but are not limited to, blood clots in the veins, thrombophlebitis, disseminated intravascular coagulation, jaundice, low blood sugar, pleural effusion, pulmonary emboli, severe ascites, or combinations thereof. Symptoms associated with a cancer are often related to tumor size and prevalence. Often, the later the stage of cancer, the more the symptoms associated with the cancer manifest within a patient.

Treatment using genetically modified stem cells may increase cancer cell death. Cancer cell death may be increased by about 10% to about 25%, about 10% to about 50%, about 20% to about 90%. Cancer cell death may be increased by at least 5%, at least 10%, at least 20%, at least 30%, at least 40%, at least 50%, at least 60%, at least 70%, at least 80%, at least 90%, at least 95%, or greater than 95%

Treatment using genetically modified stem cells in some instances decrease tumor size. Sometimes tumor size decreases by at least about 10% to about 25%, about 10% to about 50%, about 20% to about 100%. In some instances, tumor size decreases by at least 5%, at least 10%, at least 20%, at least 30%, at least 40%, at least 50%, at least 60%, at least 70%, at least 80%, at least 90%, at least 95%, or greater than 95%. Tumor size in some cases decreases by 5-95%, 10-90%, 20-80%, 30-70%, 40-60%, 50-95%, 65-85%, or 75-95%. In some cases, the decrease in tumor size is by at least 5%, 10%, 15%, 20%, 25%, 30%, 35%, 40%, 45%, 50%, 55%, 60%, 65%, 70%, 75%, 80%, 85%, 90%, 95%, or greater than 95%. The decrease in tumor size sometimes is at least 5%. In some cases, the decrease in tumor size is by at least 10%. The decrease in tumor size in some cases is at least 30%. In some instances, the decrease in tumor size may be by at least 50%.

In some instances, reduction in cancer is measured as an increase in long term survival compared to patients not treated with genetically modified stem cells alone or in combination with surgery, chemotherapy, or radiation. Sometimes long term survival increases by 5-95%, 10-90%, 20-80%, 30-70%, 40-60%, 50-95%, 65-85%, or 75-95%. Long term survival in some cases increases by at least 5%, 10%, 15%, 20%, 25%, 30%, 35%, 40%, 45%, 50%, 55%, 60%, 65%, 70%, 75%, 80%, 85%, 90%, 95%, or greater than 95%.

The reduction in cancer in some cases is a decrease in cancer metastases. Cancer metastases may decrease by about 5-95%, 10-90%, 20-80%, 30-70%, 40-60%, 50-95%, 65-85%, or 75-95%. The decrease in cancer metastases may by at least 5%, 10%, 15%, 20%, 25%, 30%, 35%, 40%, 45%, 50%, 55%, 60%, 65%, 70%, 75%, 80%, 85%, 90%, 95%, or greater than 95%. The decrease in cancer metastases may by at least 5%. The decrease in cancer metastases may by at least 10%. The decrease in cancer metastases may by at least 30%. The decrease in cancer metastases may be by at least 50%.

Turning to the figures, one observes the following:

FIG. 1 depicts adenovirus 5 vector expression cassette. An adenovirus 5 vector contains human IL-12 and iCasp9. The expression cassette contains two inverted terminal repeats (ITR) at each end of the expression cassette. The expression cassette also contains a human cytomegalovirus (hCMV) promoter upstream of iCaspase9 gene. A hemagglutinin (HA) tag is downstream of iCaspase9. The expression cassette contains an hCMV promoter upstream the IL-12 subunits, p40 (hIL-12p40) and p35 (hIL-12p35), that are separated by a linker. The linker peptide is derived from human elastin and allows for expression of bioactive IL-12 as a single peptide. This figure demonstrates an exemplary expression cassette for transforming MSCs to express an anti-tumor agent and an apoptotic agent.

Figure 2A:
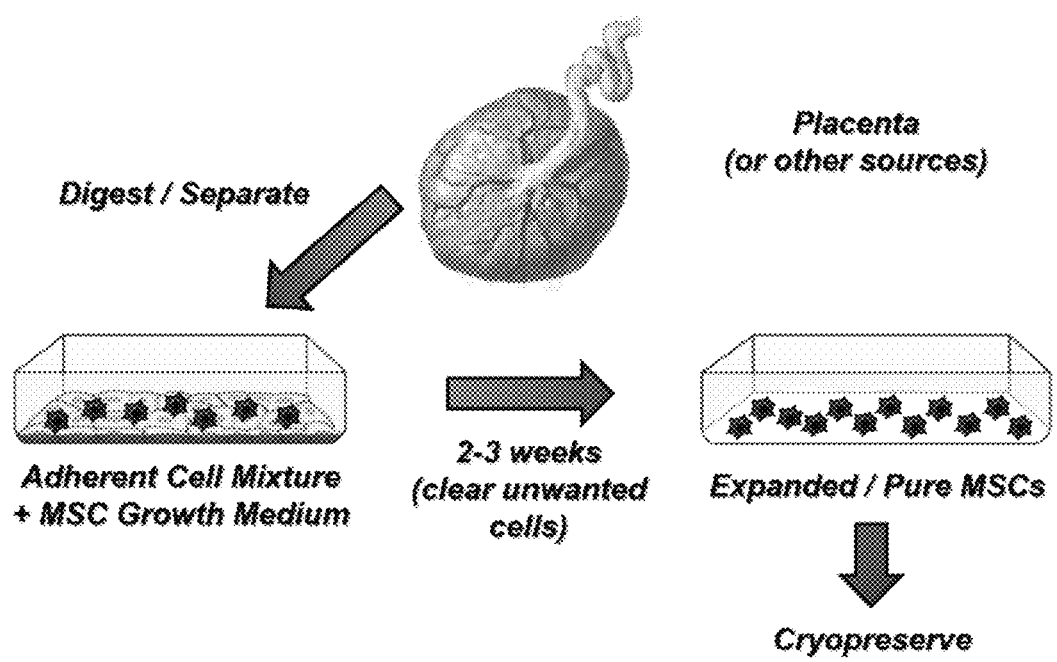
FIG. 2A depicts a first schematic of isolation of mesenchymal stem cells (MSCs) from tissue.

FIG. 2A depicts a process workflow for generation of MSCs that are derived from human bone marrow or placenta. Bone marrow or placenta is isolated, and tissue is digested. A cell mixture is then grown in MSC growth medium for 2-3 weeks in which unwanted cells are removed. Length of time for growth can depend on a donor. Pure MSCs are then expanded and are cryopreserved. This demonstrates isolation of stem cells from tissue and generation of human MSCs for subsequent gene modification.

Figure 2B:
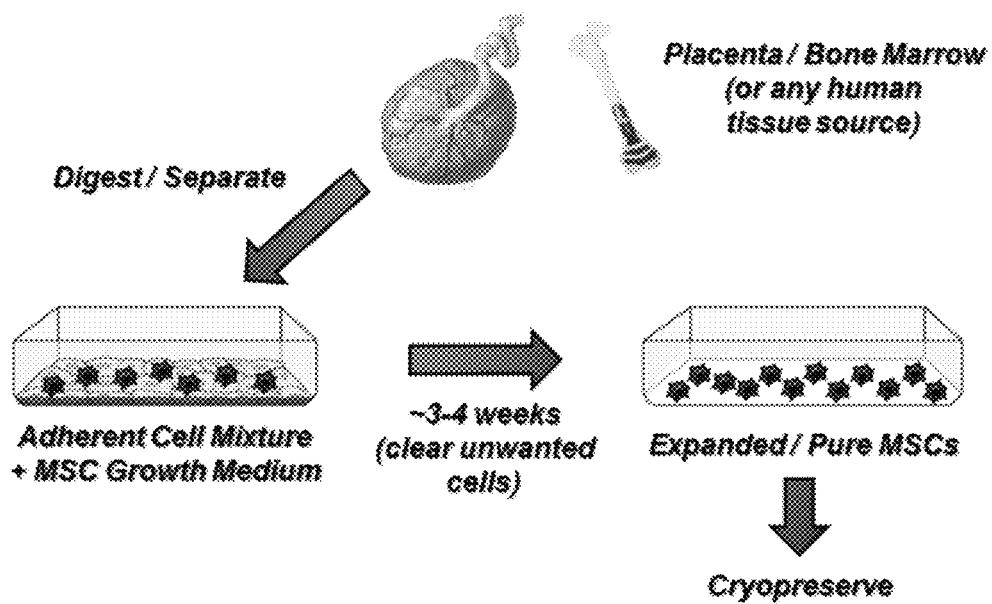
FIG. 2B depicts a second schematic of isolation of mesenchymal stem cells (MSCs) from tissue.

FIG. 2B depicts a process workflow for generation of MSCs that are derived from human bone marrow or placenta. Bone marrow or placenta is isolated, and tissue is digested. A cell mixture is then grown in MSC growth medium for 3-4 weeks in which unwanted cells are removed. Length of time for growth can depend on a donor. Pure MSCs are then expanded and are cryopreserved. This demonstrates isolation of stem cells from tissue and generation of human MSCs for subsequent gene modification.

Figure 3A:
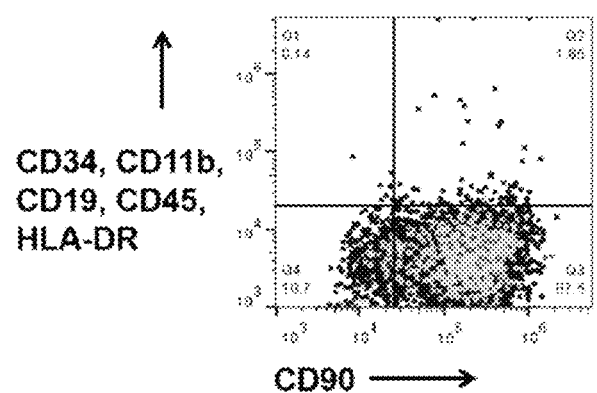
FIGS. 3A-3D depict flow cytometry graphs of phenotypical analysis of MSCs.
Figure 3B:
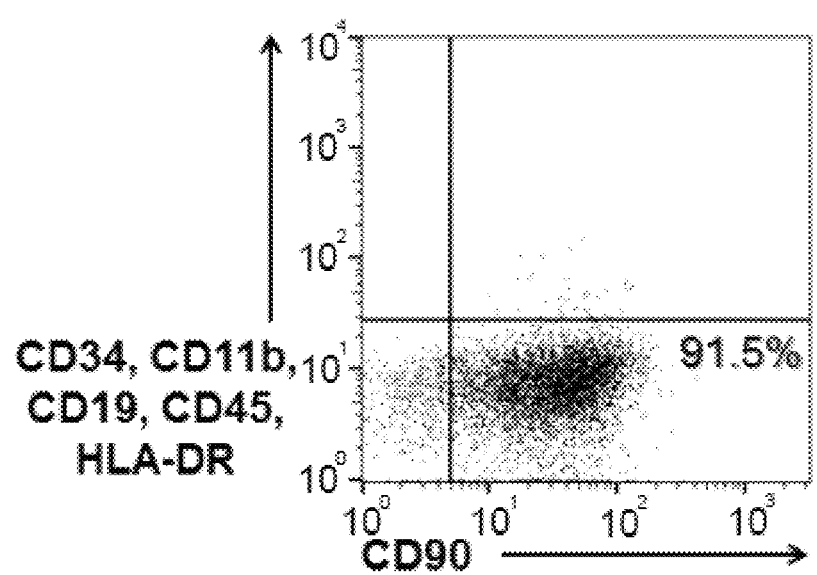
Figure 3C:
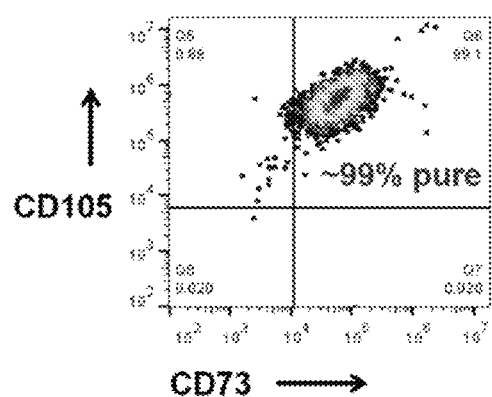
Figure 3D:
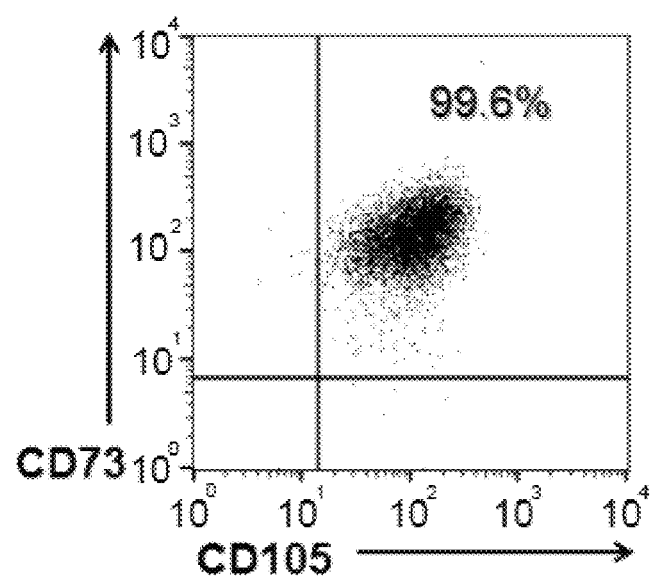

FIGS. 3A-3D depict flow cytometry graphs of pure MSCs using surface markers CD34, CD11b, CD19, CD45, HLA-DR, CD90, CD105, and CD73. The graph in FIG. 3A has a X and Y axis from $10^3$ to $10^6$. Referring to FIG. 3A, 0.14% of MSCs are found in Q1 (quadrant 1) in the top left, 1.65% of MSCs are found in Q2 (quadrant 2) in the top right, 87.5% of MSCs are found in Q3 (quadrant 3) in the bottom right, and 10.7% of MSCs are found in Q4 (quadrant 4) in the bottom left (FIG. 3A). Referring to FIG. 3B, 91.5% of cells express CD90. The graph in FIG. 3B has a X axis from $10^0$ to $10^3$ and Y axis from $10^0$ to $10^4$. Using markers, CD73 and CD105, MSCs are sorted (FIG. 3C). The graph in FIG. 3C has an X and Y axis from $10^2$ to $10^7$. Referring to FIG. 3C, 0.88% of MSCs are found in Q5 (quadrant 5) in the top left quadrant, 99.1% of MSCs are found in in Q6 (quadrant 6) in the top right quadrant, 0.020% of MSCs are found in Q7 (quadrant 7) in the bottom right, and 0.020% of MSCs are found in Q8 (quadrant 8) in the bottom left. Referring to FIG. 3D, the graph has an X from $10^0$ to $10^4$ and Y axis from $10^0$ to $10^4$. Using MSC markers, CD73 and CD105, MSCs were sorted to generate more than a 99% pure population of MSCs (FIG. 3D). These figures demonstrate identification of pure population of MSCs using surface markers expressed on cells.

Figure 4:
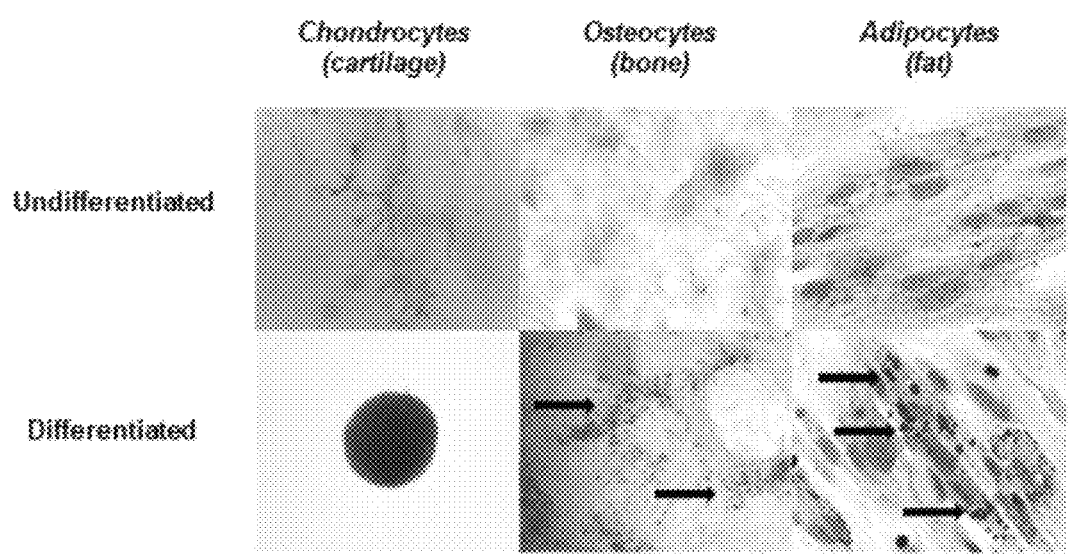
FIG. 4 depicts phenotypical identification of MSCs using cell differentiation assays.

FIG. 4 depicts images of cell differentiation assays of MSCs. Chondrocytes (left panels), osteocytes (middle panels), and adipocytes (right panels) between undifferentiated (top panels) and differentiated MSCs (bottom panels) are compared (FIG. 4). Differentiated chondrocytes (bottom left panel), osteocytes (bottom middle panel), and adipocytes (bottom right panel) exhibit changed cellular morphology compared to undifferentiated chondrocytes (upper left panel), osteocytes (upper middle panel), and adipocytes (upper right panel). Differentiated chondrocytes (bottom left panel) are confirmed by staining with Alcian Blue, which reacts with glycosaminoglycans in cartilage. Differentiated osteocytes (bottom middle panel) are confirmed by staining with Alizarin Red, which reacts to calcium deposits in bone. Differentiated adipocytes (bottom right panel) are confirmed by staining with Oil Red-O, which reacts with intra-cytoplasmic lipids. This figure demonstrates identification of MSCs by their ability to differentiate into chondrocytes, osteocytes, and adipocytes.

Figure 5:
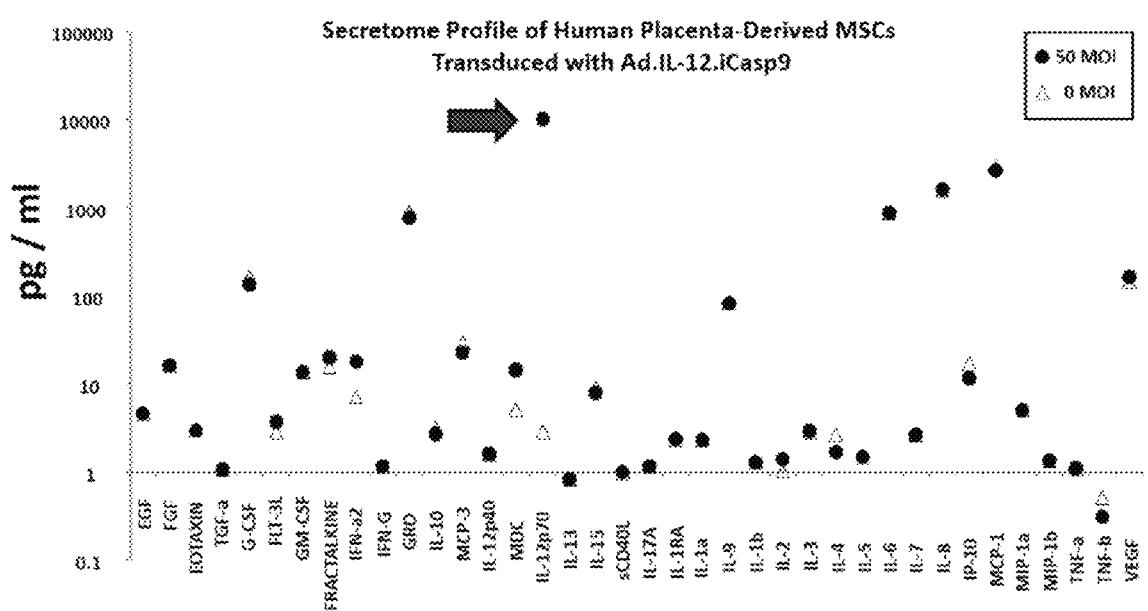
FIG. 5 depicts a graph of production of different cytokines, chemokines, and other molecules by MSCs transformed with Ad.IL.12.iCasp9.

FIG. 5 depicts a graph measuring production of human IL-12 (IL-12p70) from human placenta-derived MSCs. MSCs are transformed for 24 hours using Ad.IL-12p70 with either 0 multiplicity of infection (MOI) (open triangles) or 50 MOI (closed circles) for 24 hours. MOI refers to a ratio of viral particles to MSCs. X axis depicts EGF, FGF, eotaxin, TGFa, G-CSF, FLT-3L, GM-CSF, Fractalkine, IFN-a2, IFN-G, GRO, IL-10, MCP-3, IL-12p40, MDC, IL-12p70, IL-13, IL-15, sCD40L, IL-17A, IL-1RA, IL-1a, IL-9, IL-1b, IL-2, IL-3, IL-4, IL-5, IL-6, IL-7, IL-8, IP-10, MCP-1, MIP-1a, MIP-1b, TNF-a, TNF-b, and VEGF. Y axis depicts pg/mL (pictograms/milliliter) from −0.1 to 10,000. The graph depicts IL-12p70 in pg/mL secreted from MSCs as indicated by an arrow, which is 2000 fold higher than unmodified MSCs. This figure demonstrates that genetically modified MSCs secrete high levels of IL-12.

Figure 6:
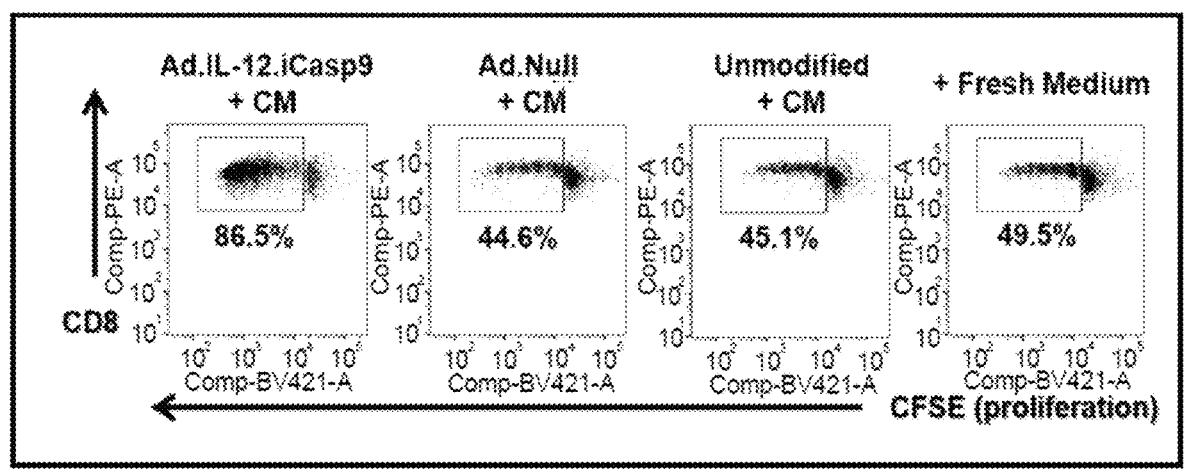
FIG. 6 depicts flow cytometry graphs of proliferation of CD8$^+$ T cells treated with fresh medium, conditioned medium from unmodified MSCs (unmodified+CM), conditioned medium from MSCs transformed with null adenovirus (Ad.Null+CM), and conditioned medium from MSCs transformed with Ad.IL.12.iCasp9 (Ad.IL-12.iCasp9+CM).

FIG. 6 depicts flow cytometry graphs of proliferation of CD8$^+$ T cells. Cells are either treated with fresh medium, conditioned media from unmodified MSCs (unmodified+CM), conditioned media from MSCs transformed with null adenovirus (Ad.Null+CM), or conditioned media from MSCs transformed using Ad. IL-12 iCasp9 (Ad.IL-12.iCasp9+CM). Proliferation was then measured by flow cytometry. Treatment with conditioned media from Ad. IL-12 iCasp9 transformed MSCs resulted in an 86.5% proliferation of CD8$^+$ T cells, which was enhanced as compared to the other treatment conditions. CD8$^+$ T cells treated with fresh medium exhibit 49.5% proliferation. CD8$^+$ T cells treated with conditioned media from unmodified MSCs exhibited 45.1% proliferation. CD8$^+$ T cells treated with conditioned media from MSCs transformed with null adenovirus exhibited 44.6% proliferation. X axis has a scale from $10^2$ to $10^5$ and Y axis scale of $10^1$ to $10^5$. This figure demonstrates that genetically modified MSCs secrete factors into the media that stimulate CD8$^+$ T cell proliferation.

Figure 7:
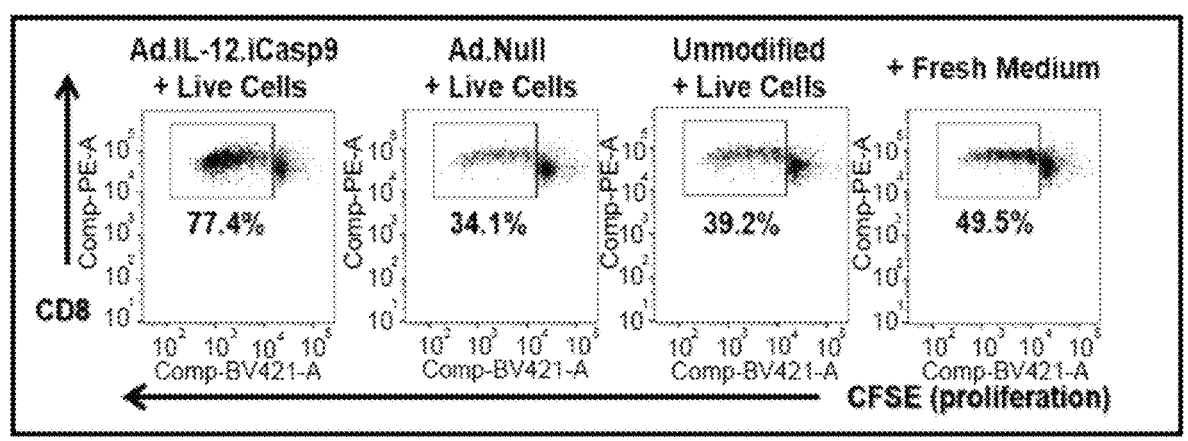
FIG. 7 depicts flow cytometry graphs of proliferation of CD8$^+$ T cells co-cultured in fresh medium, co-cultured with unmodified MSCs (unmodified+live cells), co-cultured with MSCs transformed with null adenovirus (Ad.Null+live cells), and co-cultured with MSCs transformed with Ad.IL.12.iCasp9 (Ad.IL-12.iCasp9+live cells).

FIG. 7 depicts flow cytometry graphs of proliferation of CD8$^+$ T cells co-cultured with fresh medium, unmodified MSCs (unmodified+live cells), MSCs transformed with null adenovirus (Ad.Null+live cells), or Ad. IL-12 iCasp9 transformed MSCs (Ad.IL-12.iCasp9+live cells). Co-culture of CD8$^+$ T cells with Ad. IL-12 iCasp9 transformed MSCs exhibit 77.4% proliferation of CD8$^+$ T cells, which is enhanced as compared to the other treatment conditions. CD8$^+$ T cells treated with fresh medium exhibit 49.5% proliferation. CD8$^+$ T cells co-cultured with unmodified MSCs exhibit 39.2% proliferation. CD8$^+$ T cells co-cultured with MSCs transformed with null adenovirus exhibit 34.1% proliferation. X axis has a scale from $10^2$ to $10^5$ and Y axis scale of $10^1$ to $10^5$. This figure demonstrates that genetically modified MSCs stimulate CD8$^+$ T cell proliferation.

Figure 8:
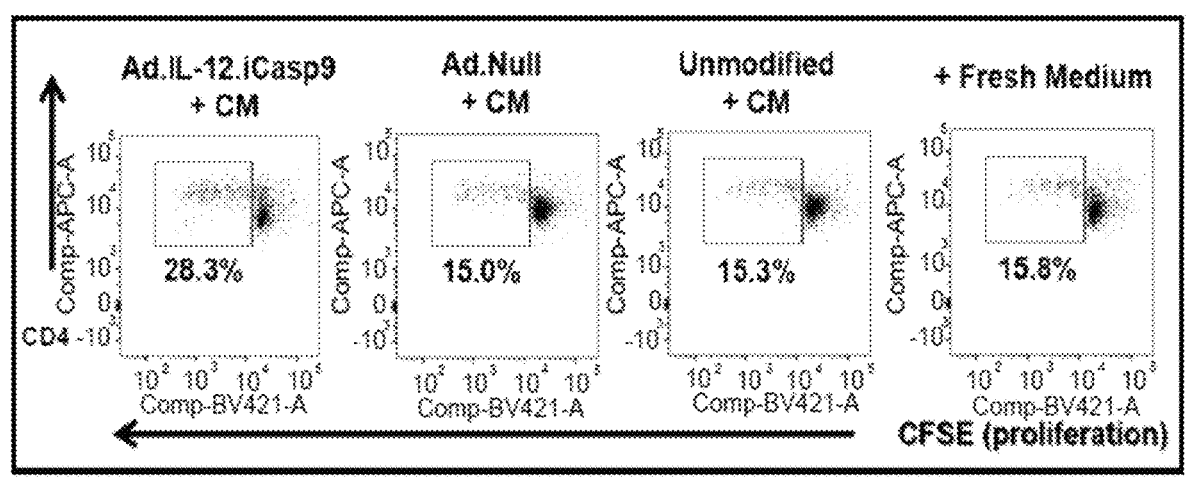
FIG. 8 depicts flow cytometry graphs of proliferation of CD4$^+$ T cells treated with fresh medium, conditioned medium from unmodified MSCs (unmodified+CM), conditioned medium from MSCs transfected with null adenovirus (Ad.Null+CM), and conditioned medium from MSCs transfected with Ad.IL.12.iCasp9 (Ad.IL-12.iCasp9+CM).

FIG. 8 depicts flow cytometry graphs of proliferation of CD4$^+$ T cells treated with fresh medium, conditioned media from unmodified MSCs (unmodified+CM), conditioned media from MSCs transformed with null adenovirus (Ad.Null+CM), or conditioned media from MSCs transformed using Ad. IL-12 iCasp9 (Ad.IL-12.iCasp9+CM). Treatment with conditioned media from Ad. IL-12 iCasp9 transformed MSCs result in a 28.3% proliferation of CD4$^+$ T cells, which is enhanced as compared to the other treatment conditions. CD4$^+$ T cells from fresh medium exhibit 15.8% proliferation. CD4$^+$ T cells treated with conditioned media from unmodified MSCs exhibit 15.3% proliferation. CD4$^+$ T cells treated with conditioned media from MSCs transformed with null adenovirus exhibit 15.0% proliferation. X axis has a scale from $10^2$ to $10^5$ and is labeled Comp-PE-A. Y axis has a scale of $-10^3$ to $10^5$ and is labeled Comp-BV421-A. This figure demonstrates that genetically modified MSCs secrete factors into the media that stimulate CD4$^+$ T cell proliferation.

Figure 9:
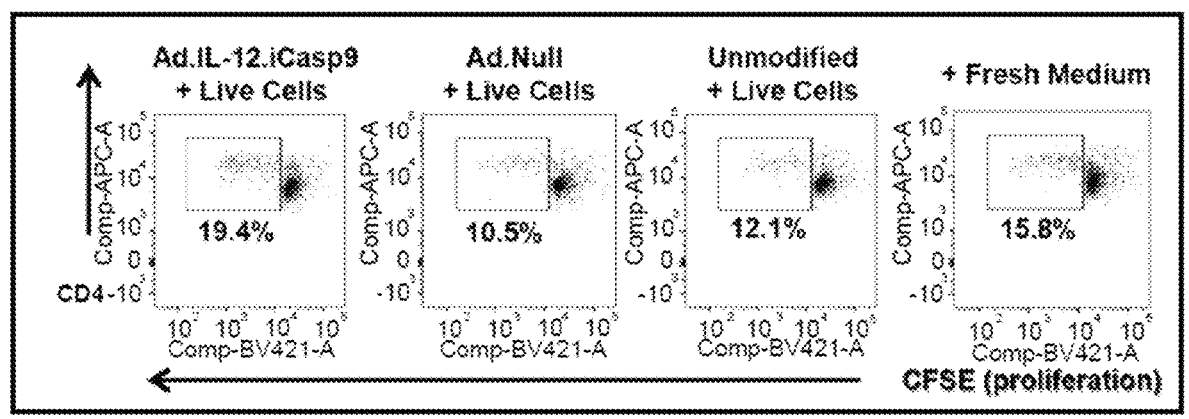
FIG. 9 depicts flow cytometry graphs of proliferation of CD4$^+$ T cells co-cultured in fresh medium, co-cultured with unmodified MSCs (unmodified+live cells), co-cultured with MSCs transfected with null adenovirus (Ad.Null+live cells), and co-cultured with MSCs transformed with Ad.IL.12.iCasp9 (Ad.IL-12.iCasp9+live cells).

FIG. 9 depicts flow cytometry graphs of proliferation of CD4$^+$ T cells co-cultured with fresh medium, unmodified MSCs (unmodified+live cells), MSCs transformed with null adenovirus (Ad.Null+live cells), or Ad. IL-12 iCasp9 transformed MSCs (Ad.IL-12.iCasp9+live cells). Co-culture of CD4$^+$ T cells with Ad. IL-12 iCasp9 transformed MSCs exhibit 19.4% proliferation of CD4$^+$ T cells, which was enhanced as compared to the other treatment conditions. CD4$^+$ T cells treated with fresh medium exhibit 15.8% proliferation. CD4$^+$ T cells co-cultured with unmodified MSCs exhibit 12.1% proliferation. CD4$^+$ T cells co-cultured with MSCs transformed with null adenovirus exhibit 10.5% proliferation. X axis has a scale from $10^2$ to $10^5$ and is labeled Comp-PE-A. Y axis has a scale of $-10^3$ to $10^5$ and is labeled Comp-BV421-A. This figure demonstrates that genetically modified MSCs stimulate CD4$^+$ T cell proliferation.

Figure 10:
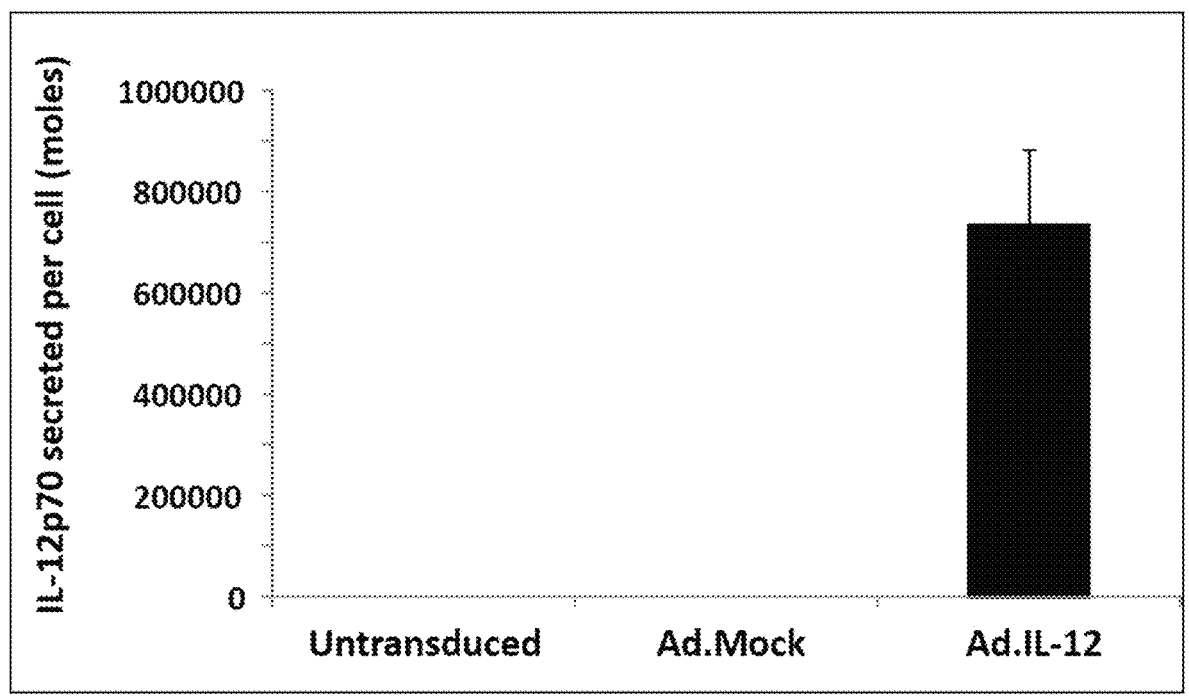
FIG. 10 depicts a graph of production of human IL-12 from human placenta derived MSCs transduced with null virus (Ad.Mock) or Ad.IL-12.iCasp9 (Ad.IL-12) compared to MSCs that are untransduced. Y-axis is moles of IL-12p70 secreted from cells.

FIG. 10 depicts a graph of production of human IL-12 from human placenta derived MSCs transduced with null virus (Ad.Mock) or Ad.IL-12.iCasp9 (Ad.IL-12) compared to MSCs that are untransduced. Y-axis is moles of IL-12p70 secreted from cells and has a scale from 0 to 1000000 moles.

Figure 11A:
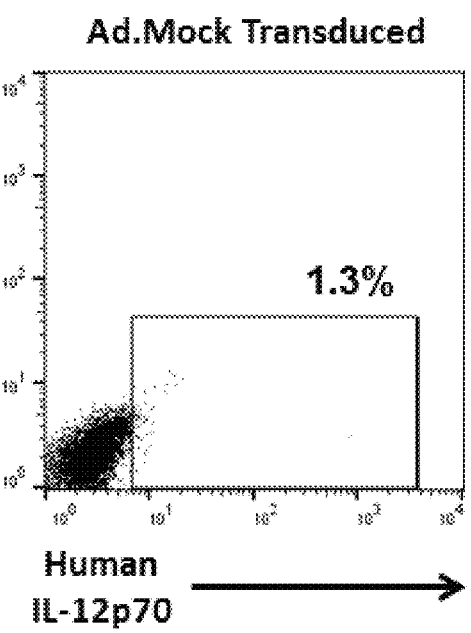
FIGS. 11A-11B depict flow cytometry graphs of human IL-12p70 expression in human placenta-derived MSCs transduced for 48 hours with null virus (Ad.Mock) or Ad.IL-12.iCasp9 (Ad.IL-12).
Figure 11B:
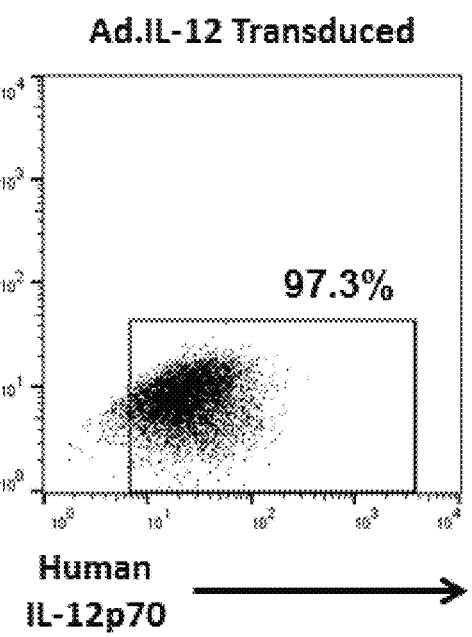

FIGS. 11A-11B depict flow cytometry graphs of human IL-12p70 expression in human placenta-derived MSCs transduced for 48 hours with null virus (Ad.Mock) or Ad.IL-12.iCasp9 (Ad.IL-12). MSCs transduced with null virus exhibit 1.3% proliferation (FIG. 11A). MSCs transduced with Ad.IL-12 exhibit 97.3% proliferation (FIG. 11B). X axis has a scale from $10^0$ to $10^4$ and Y axis scale of $10^0$ to $10^4$.

Figure 12:
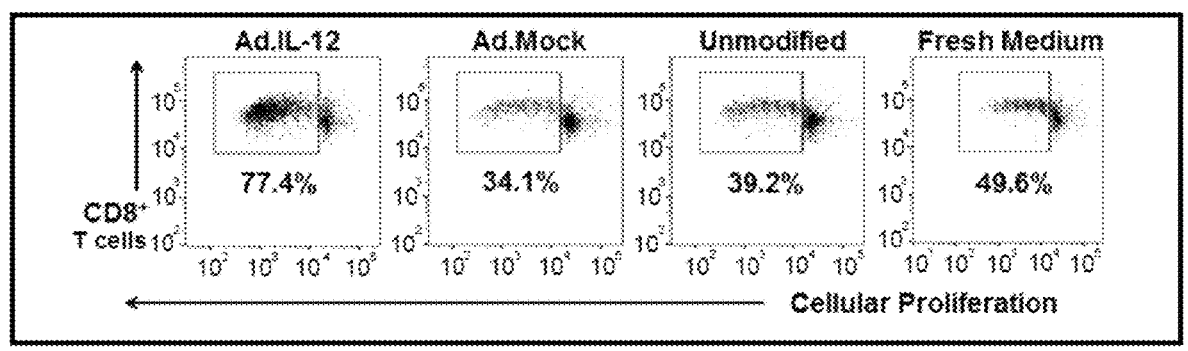
FIG. 12 depicts flow cytometry graphs of proliferation of CD8$^+$ T cells that are treated with human placenta-derived MSCs. Conditions include fresh medium, unmodified MSCs (unmodified), MSCs transformed with null adenovirus (Ad.Mock), and MSCs transformed with Ad.IL-12 (Ad.IL-12).

FIG. 12 depicts flow cytometry graphs of proliferation of CD8+ T cells that were treated with human placenta-derived MSCs. Conditions include fresh medium, unmodified MSCs (unmodified), MSCs transformed with null adenovirus (Ad-.Mock), and MSCs transformed with Ad.IL-12 (Ad.IL-12). MSCs treated with fresh medium exhibit 49.6% proliferation. Unmodified MSCs exhibit 39.2% proliferation. MSCs transformed with null adenovirus (Ad.Mock) exhibit 34.1% proliferation. MSCs transformed with Ad.IL-12 (Ad.IL-12) exhibit 77.4% proliferation. X axis has a scale from $10^2$ to $10^5$ and Y axis scale of $10^1$ to $10^5$.

Figure 13:
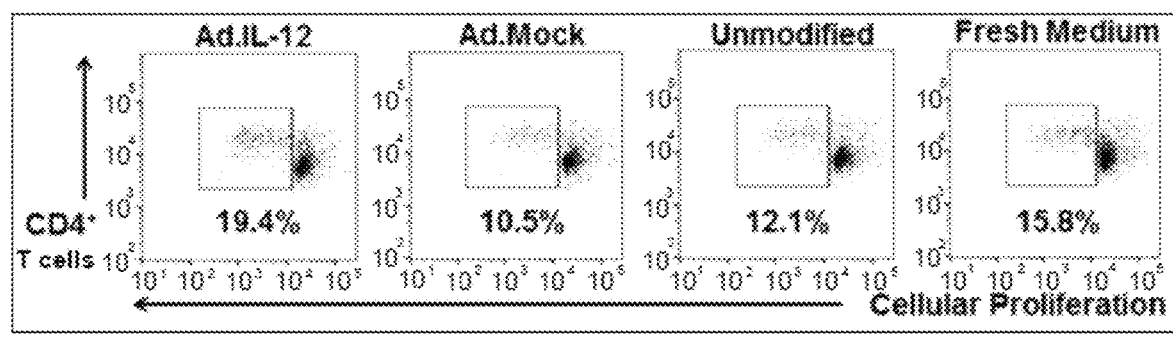
FIG. 13 depicts flow cytometry graphs of proliferation of CD4$^+$ T cells that are treated with human placenta-derived MSCs. Conditions include fresh medium, unmodified MSCs (unmodified), MSCs transformed with null adenovirus (Ad.Mock), and MSCs transformed with Ad.IL-12 (Ad.IL-12).

FIG. 13 depicts flow cytometry graphs of proliferation of CD4+ T cells that were treated with human placenta-derived MSCs. Conditions include fresh medium, unmodified MSCs (unmodified), MSCs transformed with null adenovirus (Ad-.Mock), and MSCs transformed with Ad.IL-12 (Ad.IL-12). MSCs treated with fresh medium exhibit 15.8% proliferation. Unmodified MSCs exhibit a 12.1% proliferation. MSCs transformed with null adenovirus (Ad.Mock) exhibit 10.5% proliferation. MSCs transformed with Ad.IL-12 (Ad.IL-12) exhibit 19.4% proliferation. X axis has a scale from $10^2$ to $10^5$ and Y axis scale of $10^1$ to $10^5$.

Figure 14:
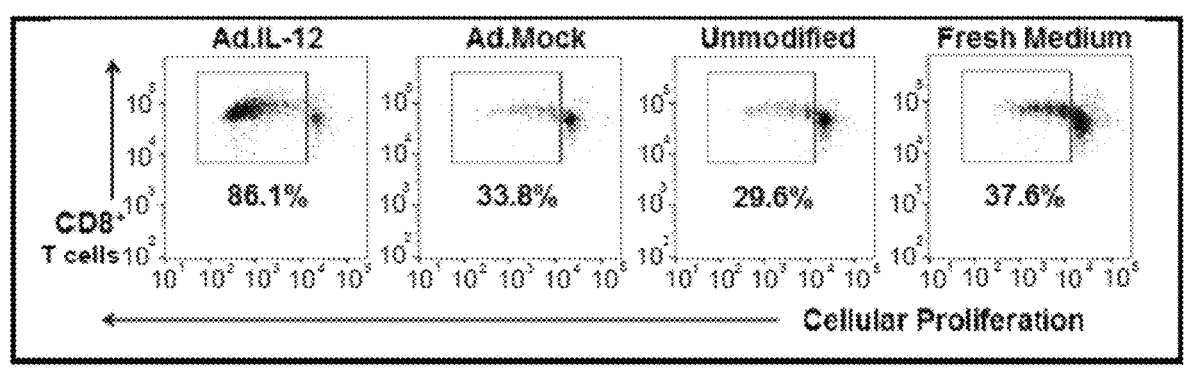
FIG. 14 depicts flow cytometry graphs of proliferation of CD8$^+$ T cells that are treated with human bone marrow-derived MSCs. Conditions include fresh medium, unmodified MSCs (unmodified), MSCs transformed with null adenovirus (Ad.Mock), and MSCs transformed with Ad.IL-12 (Ad.IL-12).

FIG. 14 depicts flow cytometry graphs of proliferation of CD8+ T cells that were treated with human bone marrow-derived MSCs. Conditions include fresh medium, unmodified MSCs (unmodified), MSCs transformed with null adenovirus (Ad.Mock), and MSCs transformed with Ad.IL-12 (Ad.IL-12). MSCs treated with fresh medium exhibit a 37.6% proliferation. Unmodified MSCs exhibit a 29.6% proliferation. MSCs transformed with null adenovirus (Ad-.Mock) exhibit 33.8% proliferation. MSCs transformed with Ad.IL-12 (Ad.IL-12) exhibit 86.1% proliferation. X axis has a scale from $10^2$ to $10^5$ and Y axis scale of $10^1$ to $10^5$.

Figure 15:
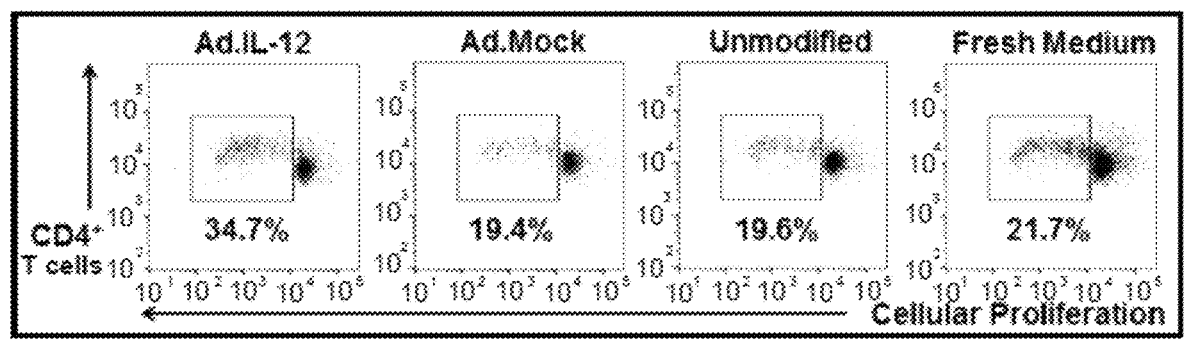
FIG. 15 depicts flow cytometry graphs of proliferation of CD4$^+$ T cells that are treated with human bone marrow-derived MSCs. Conditions include fresh medium, unmodified MSCs (unmodified), MSCs transformed with null adenovirus (Ad.Mock), and MSCs transformed with Ad.IL-12 (Ad.IL-12).

FIG. 15 depicts flow cytometry graphs of proliferation of CD4+ T cells that were treated with human bone marrow-derived MSCs. Conditions include fresh medium, unmodified MSCs (unmodified), MSCs transformed with null adenovirus (Ad.Mock), and MSCs transformed with Ad.IL-12 (Ad.IL-12). MSCs treated with fresh medium exhibit a 21.7% proliferation. Unmodified MSCs exhibit a 19.6% proliferation. MSCs transformed with null adenovirus (Ad-.Mock) exhibit 19.4% proliferation. MSCs transformed with Ad.IL-12 (Ad.IL-12) exhibit 34.7% proliferation. X axis has a scale from $10^2$ to $10^5$ and Y axis scale of $10^1$ to $10^5$.

These figures demonstrate that pure populations of MSCs can be isolated, genetically modified using an adenovirus comprising IL-12 and iCasp9, and subsequently affect T cell responses.

Definitions

Unless otherwise defined, all technical terms used herein have the same meaning as commonly understood by one of ordinary skill in the art to which this invention belongs.

The term "stem cell" as used herein refers to an undifferentiated cell of a multicellular organism that is capable of giving rise to indefinitely more cells of the same type, and from which certain other kinds of cell arise by differentiation. A cell of a multicellular organism of the present application may be any type of eukaryotic cell, for example a mammalian cell, for example a dog, cat, cow, sheep, ferret, or human cell The term "transform" and its grammatical equivalents as used herein refer to the process by which foreign DNA or a part thereof is introduced into a cell. In some instances, transformation is made through adenovirus, lentivirus, or adeno-associated virus.

The term "adenovirus" or "Ad" refers to a group of non-enveloped DNA viruses from the family Adenoviridae. In addition to human hosts, these viruses can be found in, but are not limited to, avian, bovine, porcine and canine species.

The term "anti-tumor agent" as used herein is defined as an agent that diminishes the size of a tumor or eliminates a tumor site.

The term "apoptotic agent" as used herein refers to an agent that promotes cell death. To control the action of the apoptotic agent, the apoptotic agent is preferably inducible.

As used herein the term "antibody" refers to, but not limited to, a monoclonal antibody, a synthetic antibody, a polyclonal antibody, a multispecific antibody (including a bi-specific antibody), a human antibody, a humanized antibody, a chimeric antibody, a single-chain Fvs (scFv) (including bi-specific scFvs), a single chain antibody, a Fab fragment, a F(ab') fragment, a disulfide-linked Fvs (sdFv), or an epitope-binding fragment thereof. In some cases, the antibody is an immunoglobulin molecule or an immunologically active portion of an immunoglobulin molecule. In some instances, an antibody is animal in origin including birds and mammals. Alternately, an antibody is human or a humanized monoclonal antibody.

As used herein, the term "effective amount" or "therapeutic effective amount" refers to the amount of a compound described herein that is sufficient to effect the intended application including but not limited to disease treatment, as defined below. The therapeutically effective amount may vary depending upon the intended application (in vitro or in vivo), or the subject being treated, e.g., the weight and age of the subject, the severity of the disease condition, the manner of administration and the like, which can readily be determined by one of ordinary skill in the art. The specific dose will vary depending on the particular compounds chosen, the dosing regimen to be followed, timing of administration, or the physical delivery system in which it is carried.

As used herein, "treatment," "treating," and their grammatical equivalents is used to refer to an approach for obtaining beneficial or desired results including but not limited to therapeutic benefit and/or a prophylactic benefit. By therapeutic benefit is meant reduction, eradication or amelioration of the underlying disorder being treated. Also, a therapeutic benefit is achieved with the reduction eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

As used herein "chemotherapy" refers to treatment using a drug such as a chemical compound to stop growth of cancer cells by killing cancer cells or stopping cancer cell division.

As used herein, the term "radiation" refers to therapy involving high-energy radiation to shrink tumors and kill cancer cells. Non-limiting examples of radiation sources are X-rays, gamma rays, neutrons, and protons.

The term "subject" as used herein includes any member of the animal kingdom, including humans.

The term "protein" as used herein refers to any polymeric chain of amino acids linked by sequential peptide bonds, and is generally synonymous with "polypeptide." The term "protein" encompasses native or modified protein, protein fragments, polypeptide analogs comprising non-native amino acid residues, or portions thereof. In some instances, a protein is monomeric. In other instances, a protein is polymeric. In some instances, the amino acid sequence is one that occurs in nature. In other instances, the amino acid sequence is engineered by humans. The amino acids may be the L-optical isomer or the D-optical isomer. A polypeptide can be a chain of at least three amino acids, peptidemimetics, a protein, a recombinant protein, an antibody (monoclonal or polyclonal), an antibody fragment, a single-chain variable fragment (scFv), an antigen, an epitope, an enzyme, a receptor, a vitamin, or a structure analogue or combinations thereof. A polypeptide chain may vary in length. As used herein, the abbreviations for the L-enantiomeric and D-enantiomeric amino acids that form a polypeptide are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). X or Xaa can indicate any amino acid. In some instances, a protein is defined by its activity. For example, a protein comprises a protein that has a biological function or biological effect comparable to the corresponding native protein. In the context of proteins this typically means that a polynucleotide or polypeptide comprises a biological function or effect that has at least about 20%, about 50%, about 60%, about 70%, about 75%, about 80%, about 85%, about 90%, about 95%, about 98% or 100% biological function compared to the corresponding native protein using standard parameters. Assays that can be utilized to determine protein activity are known in the art.

As used herein, the term "homology" refers to percent sequence identity between a particular nucleic acid or amino acid sequence and another nucleic acid or amino acid sequence.

As used herein, the term "comprising" and its grammatical equivalents specifies the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

INCORPORATION BY REFERENCE

All publications, patents, and patent applications mentioned in this specification are herein incorporated by reference to the same extent as if each individual publication, patent, or patent application was specifically and individually indicated to be incorporated by reference.

EXAMPLES

The following examples are illustrative and non-limiting to the scope of the compositions and methods described herein.

Example 1: Generation and Characterization of Human Mesenchymal Stem Cell Lines

Bone marrow or placenta was isolated and digested. The cell mixture was then grown in mesenchymal stem cell (MSC) growth medium for 2-3 weeks in which unwanted cells were removed (FIG. 2A) or for 3-4 weeks (FIG. 2B). Pure MSCs were expanded and phenotypically identified by flow cytometry using surface markers on the MSCs such as CD34, CD11b, CD19, CD45, HLA-DR, CD90, CD105, and CD73 (FIGS. 3A-3D). MSCs were identified for expression of CD90 and lack of expression of CD34, CD11b, CD19, CD45, and HLA-DR (FIGS. 3A-3B). In a first experiment, 87.5% of MSCs showed high expression of CD90 and low expression of CD34, CD11b, CD19, CD45, HLA-DR (FIG. 3A). In a second experiment, 91.5% of MSCs showed high expression of CD90 and low expression of CD34, CD11b, CD19, CD45, HLA-DR (FIG. 3B). Using MSC markers, CD73 and CD105, MSCs were sorted to generate more than a 95% pure population of MSCs (FIGS. 3C-3D).

Pure MSCs were identified using cell differentiation assays (FIG. 4). The ability to differentiate into chondrocytes, osteocytes, and adipocytes was used to identify human MSCs. Chondrocytes (left panels), osteocytes (middle panels), and adipocytes (right panels) between undifferentiated (top panels) and differentiated MSCs (bottom panels) were compared. As seen in FIG. 4, differentiated chondrocytes (bottom left panel), osteocytes (bottom middle panel), and adipocytes (bottom right panel) exhibited changed cellular morphology compared to undifferentiated chondrocytes (upper left panel), osteocytes (upper middle panel), and adipocytes (upper right panel). In addition, differentiated osteocytes (bottom middle panel) and adipocytes (bottom right panel) exhibited increased staining compared to undifferentiated osteocytes (top middle panel) and adipocytes (top right panel).

This example illustrates that MSCs were isolated from tissue and pure populations of MSCs were generated. MSCs were identified by expression of several markers and by their ability to differentiate into chondrocytes, osteocytes, and adipocytes.

Example 2: Secretion of IL-12 from MSCs

Human MSCs were transformed with an adenovirus vector containing human IL-12 gene and inducible Caspase 9 gene (iCasp9). MSCs were transformed with either 0 multiplicity of infection (MOI) or 50 MOI for 24 hours. The amount of human IL-12 (IL-12p70) from MSCs was measured as pg/mL (FIG. 5). In addition to IL-12p70, several chemokines, cytokines, and other molecules were measured (FIG. 5). These included EGF, FGF, eotaxin, TGFa, G-CSF, FLT-3L, GM-CSF, Fractalkine, IFN-a2, IFN-G, GRO, IL-10, MCP-3, IL-12p40, MDC, IL-12p70, IL-13, IL-15, sCD40L, IL-17A, IL-1RA, IL-1a, IL-9, IL-1b, IL-2, IL-3, IL-4, IL-5, IL-6, IL-7, IL-8, IP-10, MCP-1, MIP-1b, TNF-a, TNF-b, and VEGF (FIG. 5). The amount of IL-12p70 secreted from MSC was 2000 fold higher than unmodified MSCs.

This example demonstrates that MSCs transformed with an adenovirus comprising human IL-12 and iCasp9 secreted high levels of IL-12.

Example 3: Conditioned Medium from IL-12 Producing MSCs Enhanced In Vitro Proliferation Proliferation of CD8+ T cells and CD4+ T cells were measured after treatment with conditioned media (CM) from IL-12 producing MSCs.

As seen in FIG. 6, cells were either treated with fresh medium, conditioned media from unmodified MSCs (unmodified+CM), conditioned media from MSCs transformed with null adenovirus (Ad. Null+CM), or conditioned media from MSCs transformed using adenovirus with human IL-12 and iCasp9 (Ad. IL-12 iCasp9+CM). Proliferation of CD8+ T cells was then measured by flow cytometry. Treatment with conditioned media from Ad. IL-12 iCasp9 transformed MSCs resulted in an 86.5% proliferation of CD8+ T cells, which was enhanced as compared to the other treatment conditions. CD8+ T cells from fresh medium exhibited 49.5% proliferation. CD8+ T cells treated with conditioned media from unmodified MSCs exhibited 45.1% proliferation. CD8+ T cells treated with conditioned media from MSCs transformed with null adenovirus exhibited 44.6% proliferation.

Potentiated in vitro proliferation of CD4+ T cells was also observed with conditioned medium from Ad. IL-12 iCasp9 transformed MSCs (FIG. 8) Cells were either treated with fresh medium, conditioned media from unmodified MSCs (unmodified+CM), conditioned media from MSCs transformed with null adenovirus (Ad. Null+CM), or conditioned media from MSCs transformed using adenovirus with human IL-12 and iCasp9 (Ad. IL-12 iCasp9+CM). Treatment with conditioned media from Ad. IL-12 iCasp9 transformed MSCs resulted in a 28.3% proliferation of CD4+ T cells, which was enhanced as compared to the other treatment conditions. CD4+ T cells from fresh medium exhibited 15.8% proliferation. CD4+ T cells treated with conditioned media from unmodified MSCs exhibited 15.3% proliferation. CD4+ T cells treated with conditioned media from MSCs transformed with null adenovirus exhibited 15.0% proliferation.

This example illustrates that genetically modified MSCs secreted factors into the media that increased CD4+ and CD8+ T cell proliferation.

Example 4: Co-Culture with Ad.IL-12 iCasp9 Transformed MSCs Enhanced In Vitro Proliferation Cells co-cultured with Ad-IL-12 iCasp9 transformed MSCs exhibited enhanced in vitro proliferation.

CD8+ T cell proliferation was measured in cells co-cultured in fresh medium, unmodified MSCs (unmodified+live cells), MSCs transformed with null adenovirus (Ad. Null+live cells), or Ad. IL-12 iCasp9 transformed MSCs (Ad.IL-12.iCasp9+Live cells) (FIG. 7). Proliferation of CD8+ T cells was then measured by flow cytometry. Co-culture of CD8+ T cells with Ad. IL-12 iCasp9 transformed MSCs exhibited 77.4% proliferation of CD8+ T cells, which was enhanced as compared to the other treatment conditions. CD8+ T cells treated with fresh medium exhibited 49.5% proliferation. CD8+ T cells co-cultured with unmodified MSCs exhibited 39.2% proliferation. CD8+ T cells co-cultured with MSCs transformed with null adenovirus exhibited 34.1% proliferation.

CD4+ T cells also exhibited increased proliferation when co-cultured in fresh medium, unmodified MSCs (unmodified+live cells), MSCs transformed with null adenovirus (Ad. Null+live cells), or Ad. IL-12 iCasp9 transformed MSCs (Ad.IL-12.iCasp9+live cells) (FIG. 9). CD4+ T cells co-cultured with Ad. IL-12 iCasp9 transformed MSCs exhibited 19.4% proliferation of CD4+ T cells, which was enhanced as compared to the other treatment conditions. CD4+ T cells treated with fresh medium exhibited 15.8% proliferation. CD4+ T cells co-cultured with unmodified MSCs exhibited 12.1% proliferation. CD4+ T cells co-cultured with MSCs transformed with null adenovirus exhibited 10.5% proliferation.

This example illustrates that genetically modified MSCs stimulated CD4+ and CD8+ T cell proliferation.

Example 5: IL-12 Producing Human MSCs

MSCs were genetically modified and expression and effects on proliferation were measured.

Production of human IL-12 (IL-12p70) was measured from human placenta-derived MSCs. MSCs were transduced with null virus (Ad-Mock) or Ad.IL-12.iCasp9 (Ad.IL-12) for 48 hours. As seen in FIG. 10, amount of IL-12p70 in moles secreted from MSCs was measured in untransduced MSCs, MSCs transduced with null virus (Ad-Mock) or Ad.IL-12.iCasp9 (Ad.IL-12).

Expression of intracellular human IL-12p70 was measured in human placenta-derived MSCs. MSCs were transduced with null virus (Ad-Mock), or Ad.IL-12.iCasp9 (Ad.IL-12) for 48 hours and human IL-12p70 expression was measured by flow cytometry. Transduction of null virus (Ad-mock) resulted in 1.3% of MSCs expressing of human IL-12p70 (FIG. 11A) whereas transduction of Ad.IL-12p70 (Ad.IL-12) resulted in a 97.3% of MSCs expressing IL-12p70 (FIG. 11B).

Proliferation effects of human placenta-derived IL-12 MSCs were measured in CD8+ T cells. Cells were co-cultured for four days with fresh medium, unmodified MSCs (unmodified), MSCs transformed with null adenovirus (Ad.Mock), and MSCs transformed with Ad.IL-12 (Ad.IL-12). Proliferation was measured in CD8+ T cells. MSCs treated with fresh medium exhibited 49.6% proliferation. Unmodified MSCs exhibited a 39.2% proliferation. MSCs transformed with null adenovirus (Ad.Mock) exhibited 34.1% proliferation. MSCs transformed with Ad.IL-12 (Ad.IL-12) exhibited 77.4% proliferation. See FIG. 12.

Proliferation effects of human placenta-derived IL-12 MSCs were measured in CD4+ T cells. Cells were co-cultured for four days with fresh medium, unmodified MSCs (unmodified), MSCs transformed with null adenovirus (Ad.Mock), and MSCs transformed with Ad.IL-12 (Ad.IL-12). Proliferation was measured in CD4+ T cells. MSCs treated with fresh medium exhibited 15.8% proliferation. Unmodified MSCs exhibited a 12.1% proliferation. MSCs transformed with null adenovirus (Ad.Mock) exhibited 10.5% proliferation. MSCs transformed with Ad.IL-12 (Ad.IL-12) exhibited 19.4% proliferation. See FIG. 13

Proliferation effects of bone marrow placenta-derived IL-12 MSCs were measured in CD8+ T cells. Cells were co-cultured for four days with fresh medium, unmodified MSCs (unmodified), MSCs transformed with null adenovirus (Ad.Mock), and MSCs transformed with Ad.IL-12 (Ad.IL-12). Proliferation was measured in CD8+ T cells. MSCs treated with fresh medium exhibited a 37.6% proliferation. Unmodified MSCs exhibited a 29.6% proliferation. MSCs transformed with null adenovirus (Ad.Mock) exhibited 33.8% proliferation. MSCs transformed with Ad.IL-12 (Ad.IL-12) exhibited 86.1% proliferation. See FIG. 14.

Proliferation effects of bone marrow placenta-derived IL-12 MSCs were measured in $CD4^+$ T cells. Cells were co-cultured for four days with fresh medium, unmodified MSCs (unmodified), MSCs transformed with null adenovirus (Ad.Mock), and MSCs transformed with Ad.IL-12 (Ad.IL-12). Proliferation was measured in $CD4^+$ T cells. MSCs treated with fresh medium exhibited a 21.7% proliferation. Unmodified MSCs exhibited a 19.6% proliferation. MSCs transformed with null adenovirus (Ad.Mock) exhibited 19.4% proliferation. MSCs transformed with Ad.IL-12 (Ad.IL-12) exhibited 34.7% proliferation. See FIG. 15.

This example illustrates that genetically modified MSCs stimulated $CD4^+$ and $CD8^+$ T cell proliferation.

Example 6: Genetically Modified MSCs in a Mouse Model for Mesothelioma

The effect of genetically modified MSCs in a mouse model for mesothelioma is tested.

Mouse C57BL/6 mesenchymal stem cells (mMSCs) are isolated from mouse bone marrow and cultured. mMSCs are transformed with adenovirus to express the mouse interleukin-12 (mIL-12) gene. mMSCs are also transformed with adenovirus to express mIL-12 gene and mouse caspase-9 (mCasp-9) gene. The genetically modified mMSCs show increased secretion of mIL-12 in vitro. A mouse model of malignant mesothelioma, comprising of 30 mice with lesions in their mesothelial lining of the thoracic cavity, are used to study the effects of the genetically modified MSCs. One group of ten mice is injected with saline as a control. A second group of ten mice is injected at the tumor site with the genetically modified mMSCs expressing mIL-12. A third group of ten mice is injected at the tumor site with the genetically modified mMSCs expressing mIL-12 and iCasp9. By week 24 post-injection, nine mice that are injected with the genetically modified mMSCs expressing mIL-12 and nine mice that are injected with the genetically modified MSCs expressing mIL-12 and iCasp9 are alive, whereas only one mouse injected with saline is alive. Once tumor size is reduced by week 24 post-injection, mice that are injected with mMSCs expressing mIL-12 and iCasp9 are further treated with an agent to activate m-Casp9.

Tumors from the different treatment groups are excised and analyzed. Mice that are injected with the genetically modified mMSCs exhibit reduced tumor size. Immunocytochemistry analysis of the tumors also demonstrate increased immune cell infiltration in tumors excised from mice that are injected with genetically modified mMSCs as opposed to tumors from saline injected mice.

Example 7: Treatment of Patients with Cancer by Surgery

One hundred patients that are diagnosed with malignant pleural mesothelioma (MPM) as a result of asbestos exposure undergo surgery to remove the malignant tumor and are maintained on radiation and chemotherapy.

Though the tumor is excised, cancer cells are not completely removed. The radiation and chemotherapy result in a wounding response and increased proliferation of the cancer cells that remain. As a result, the tumor returns, and by 5 years post-surgery, the patients nearly all have a relapse of MPM, and there is only a 13% survival rate.

Example 8: Treatment of Patients with Genetically Modified Stem Cells Following Tumor Excision by Surgery One hundred patients that are diagnosed with malignant pleural mesothelioma (MPM) as a result of asbestos exposure undergo surgery to remove the malignant tumor. A week following surgery, genetically modified stem cells expressing IL-12 and iCasp9 are administered by intracavitary infusion to target cancer cells remaining after surgery.

After 6 months, a PET scan is performed to determine tumor reduction. Blood tests are also performed to determine reduction of circulating cancer cells. Once the tumor has been significantly reduced, AP1903 is administered to eliminate the genetically modified stem cells and prevent potential adverse effects of genetically modified stem cells.

Patients who undergo surgery and treatment with genetically modified stem cells exhibit less relapse of cancer than surgery alone. Administration of genetically modified stem cells triggers an immune response and causes clearance of cancer cells that remain in the periphery of tumor excision. Thus, there is less proliferation and wounding at the tumor site following genetically modified stem cells, and the cancer tumor does not return.

Example 9: Treatment of a Patient with Cancer by Immunotherapy

A patient is diagnosed with MPM and is treated with chimeric antigen receptor T cells (CAR-T cells) programmed to target antigens on the cancer cells of the patient. By 5 years post-treatment, 40% of the patients who undergo CAR-T cell treatment have a relapse of MPM, and have 60% survival rate.

A patient is diagnosed with MPM and is treated with CAR-T cells and chemotherapy. By 5 years post-treatment, the patient who undergoes chemotherapy and immunotherapy have a similar relapse of MPM and survival rate as a patient who receives CAR-T cell treatment.

A patient is diagnosed with MPM is treated with a checkpoint inhibitor. The checkpoint inhibitor is Ipilimumab, a monoclonal antibody inhibitor of cytotoxic T-lymphocyte-associated antigen 4 (CTLA-4). Alternatively, the checkpoint inhibitor is Nivolumab, a monoclonal antibody inhibitor of programmed death 1 (PD-1).

Though the tumor is treated with immunotherapy, cancer cells are not completely removed. Cancer cells are able to proliferate and the tumor returns. The patient who is treated with a checkpoint inhibitor also experiences relapse of MPM.

Example 10: Treatment of a Patient with Cancer by Immunotherapy and Genetically Modified Stem Cells A patient is diagnosed with MPM and is treated with CAR-T cells programmed to target antigens on the cancer cells of the patient. Following CAR-T cell treatment, genetically modified stem cells expressing IL-12 and iCasp9 are administered by intracavitary infusion to target remaining cancer cells.

After 6 months, a PET scan is performed to determine tumor reduction. Blood tests are also performed to determine reduction of circulating cancer cells. Once the tumor has been significantly reduced, AP1903 is administered to eliminate the genetically modified stem cells and prevent potential adverse effects of MSCs.

A patient who undergoes immunotherapy and treatment with genetically modified stem cells exhibits less relapse of cancer than immunotherapy alone. Administration of genetically modified stem cells elicits a potentiated immune response than CAR-T therapy alone. As a result, cancer cells are cleared from the patient.

Example 11: Treatment of Patients with IL-12

100 patients are diagnosed with melanoma and subject to IL-12 recombinant protein injection at the tumor site.

Patients receive either vehicle injections, 250 ng/kg/day of IL-12 or 500 ng/kg/day of IL-12 per treatment every three days for a week. Tumor size is monitored by PET scan, and those receiving IL-12 injection exhibit reduced tumor size. Patients who receive the higher dose of IL-12 show a greater reduction in tumor size than the lower dose or vehicle injected patients. Biopsies of injected lesions demonstrate more T cell activation and immune cell infiltration compared to biopsies from patents who receive vehicle injections. By 5 years post-surgery, 40% of the patients who undergo IL-12 therapy have a relapse of MPM, and have 60% survival rate.

Example 12: Treatment of Patients with Genetically Modified Stem Cells Expressing IL-12

100 patients are diagnosed with melanoma and are administered genetically modified stem cells expressing IL-12 by intracavitary infusion. Tumor size is monitored by PET scan, and at the end of six months, the tumor size is reduced. Biopsies of injected lesions demonstrate T cell activation and immune cell infiltration. Patients that are treated with genetically modified stem cells exhibit an activated immune response, and cancer cells are cleared. As compared to patients who receive IL-12 injections, patients who are treated with genetically modified stem cells expressing IL-12 exhibit less side effects including lower incidence of death.

Example 13: Treatment of Cancer Using Genetically Modified Mesenchymal Stem Cells The purpose of this study is to evaluate the potential efficacy of compositions comprising genetically modified MSCs derived from adult human bone marrow that is modified to express IL-12 and iCasp-9 gene on treating breast cancer. The stem cells are transplanted into patients with stage III or stage IV breast cancer through direct injection to the tumor site.

A total of 100 patients will be used for this study. Patient eligibility is listed in Table 4. Patients undergo stem cell collection and the stem cells are transformed with the human IL-12 gene and the iCasp-9 gene using adenovirus. One day later, the patients receive autologous stem cell transplantation of the genetically modified stem cells.

Out of the 100 patients receiving autologous stem cell transplantation of the genetically modified stem cells, 85 patients show alleviated symptoms of breast cancer and substantial reduction of tumor growth 6 months after treatment as determined by PET scan. Once tumor cells are nearly undetectable in the patient's body, AP1903 is administered to eliminate the genetically modified MSCs in order to mitigate the potential clinical adverse effects of the MSCs.

Example 14: Treatment of Patients with Autologous Mesenchymal Stem Cells

Autologous MSCs derived from adult human bone marrow that are genetically modified to express IL-12 and iCasp-9 gene are used to treat breast cancer patients.

A total of 100 patients will be used for this study. MSCs are isolated and genetically modified from each of the 100 patients. The MSCs are administered to patients with stage III or stage IV breast cancer during surgery. Following tumor removal, the genetically modified MSCs are administered at the site of removal.

Out of the 100 patients receiving autologous stem cell transplantation of the genetically modified stem cells, 80 patients show alleviated symptoms of breast cancer and substantial reduction of tumor growth 6 months after treatment as determined by PET scan. Once tumor cells are nearly undetectable in the patient's body, AP1903 is administered to eliminate the genetically modified MSCs in order to mitigate the potential clinical adverse effects of the MSCs.

Example 15: Treatment of Patients with Allogeneic Mesenchymal Stem Cells

Allogeneic MSCs derived from adult human bone marrow that are genetically modified to express IL-12 and iCasp-9 gene are used to treat breast cancer patients.

A total of 100 patients will be used for this study. Frozen compositions of genetically modified stem cells are thawed and administered to patients with stage III or stage IV breast cancer during surgery. Following tumor removal and within ten minutes of thawing, compositions comprising the genetically modified MSCs are administered at the site of removal.

TABLE 4

Patient Eligibility

| | |
|---|---|
| Age | 65 and under |
| Sex | Male or Female |
| Menopausal Status | Not specified |
| Performance status | Karnofsky 80-100% |
| Life expectancy | Not specified |
| Hematopoietic | Absolute neutrophil count ≥ 1,000/mm^3 and platelet count ≥ 100,000/mm^3 |
| Hepatic | SGOT or SGPT ≤ 2 times upper limit of normal and bilirubin ≤ 1.5 mg/dL |
| Renal | Creatinine ≤ 1.2 mg/dL and creatinine clearance ≥ 70 mL/min |
| Cardiovascular | LVEF ≥ 55% by MUGA or echocardiogram |
| Pulmonary | $FEV\_1$ ≥ 60% of predicted, DLCO ≥ 60% of the lower limit of predicted value, and oxygen saturation > 92% on room air |
| Cancer | Histologically confirmed breast cancer, meeting 1 of the following stage criteria:<br>    Stage IIIB or IIIC disease, wherein patients must have received prior neoadjuvant or adjuvant therapy and must have undergone lumpectomy or mastectomy or<br>    Stage IV disease, wherein patients have only 1-3 organ sites with disease involvement after induction chemotherapy, achieved at least a partial response after induction chemotherapy, and have no more than 3 lesions in the organ sites combined |
| Other | Not pregnant or nursing, negative pregnancy test, fertile patients must use effective contraception, no autoimmune disorders, no immunosuppressive condition, and no other malignancy within the past 5 years |

Out of the 100 patients receiving allogeneic stem cell transplantation of the genetically modified stem cells, more than 50% of patients show alleviated symptoms of breast cancer and substantial reduction of tumor growth 6 months after treatment as determined by PET scan. Once tumor cells are nearly undetectable in the patient's body, AP1903 is administered to eliminate the genetically modified MSCs in order to mitigate the potential clinical adverse effects of the MSCs.

Example 16: Treatment of a Patient with Cancer by IL-2 Therapy and Genetically Modified Stem Cells A patient with cancer is treated with high-dose interleukin-2 (IL-2, Proleukin) and genetically modified stem cells expressing IL-12 and iCasp-9 gene.

A total of 100 patients will be used for this study. Patients are systemically administered high-dose interleukin-2 (IL-2, Proleukin) and genetically modified stem cells by intravenous infusion. Tumor growth is monitored for several months by PET scan. Once tumor cells are nearly undetectable in the patient's body, AP1903 is administered to eliminate the genetically modified MSCs in order to mitigate the potential clinical adverse effects of the MSCs.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of reducing tumor cell regrowth at a site of solid tumor excision, comprising:
   a. introducing to the site of solid tumor excision a composition comprising cells comprising an adenoviral vector encoding (i) an anti-tumor agent, wherein the anti-tumor agent comprises a fusion gene encoding interleukin-12, wherein the fusion gene comprises IL-12p40 and IL-12p35 and (ii) an apoptotic agent comprising an inducible caspase 9, wherein the anti-tumor agent induces an immune response;
   b. administering an exogenous signal that induces the apoptotic agent to destroy the cells encoding the anti-tumor agent and the apoptotic agent at the site of solid tumor excision.

2. The method of claim 1, wherein the composition is administered following surgery.

3. The method of claim 1, wherein the solid tumor is caused by at least one of breast cancer, colon cancer, rectal cancer, lung cancer, ovarian cancer, prostate cancer, skin cancer, brain cancer, bladder cancer, endometrial cancer, kidney cancer, pancreatic cancer, thyroid cancer, mesothelioma, and melanoma.

4. The method of claim 1, wherein the cells encoding the anti-tumor agent and the apoptotic agent are stem cells.

5. The method of claim 4, wherein the stem cells are mesenchymal stem cells.

6. The method of claim 1, wherein the composition is administered during surgery.

7. A composition for targeting cancer at a site of solid tumor excision comprising an adenoviral vector encoding (i) an anti-tumor agent, wherein the anti-tumor agent comprises a fusion gene encoding interleukin-12, wherein the fusion gene comprises IL-12p40 and IL-12p35 and (ii) an apoptotic agent comprising an inducible caspase 9.

8. The method of claim 1, wherein the composition is administered following at least one of chemotherapy and radiation.

* * * * *